(12) United States Patent
Pickett et al.

(10) Patent No.: US 8,597,730 B2
(45) Date of Patent: Dec. 3, 2013

(54) SURFACE FUNCTIONALISED NANOPARTICLES

(75) Inventors: Nigel Pickett, London (GB); Mark C. McCairn, Newent (GB); Steven M. Daniels, Manchester (GB); Imrana Mushtaq, Manchester (GB); Paul Glarvey, Stockport (GB)

(73) Assignee: Nanoco Technologies Ltd. (GB)

( * ) Notice: Subject to any disclaimer, the term of this patent is extended or adjusted under 35 U.S.C. 154(b) by 1114 days.

(21) Appl. No.: 12/537,553

(22) Filed: Aug. 7, 2009

(65) Prior Publication Data

US 2010/0068522 A1    Mar. 18, 2010

Related U.S. Application Data

(60) Provisional application No. 61/088,100, filed on Aug. 12, 2008.

(30) Foreign Application Priority Data

Aug. 7, 2008    (GB) .................................. 0814458.6

(51) Int. Cl.
*B05D 7/00*    (2006.01)
(52) U.S. Cl.
USPC ............ 427/214; 427/215; 428/403; 977/774
(58) Field of Classification Search
USPC ................. 427/212, 214, 215, 220, 216, 221; 428/403, 407; 977/973, 773, 774
See application file for complete search history.

(56) References Cited

U.S. PATENT DOCUMENTS

| 2,769,838 | A | 11/1956 | Matter et al. |
| 3,524,771 | A | 8/1970 | Green |
| 4,609,689 | A | 9/1986 | Schwartz et al. |
| 6,114,038 | A | 9/2000 | Castro et al. |
| 6,207,229 | B1 | 3/2001 | Bawendi et al. |
| 6,221,602 | B1 | 4/2001 | Barbera-Guillem et al. |

(Continued)

FOREIGN PATENT DOCUMENTS

| CN | 1394599 | 2/2003 |
| EP | 1176646 | 1/2002 |

(Continued)

OTHER PUBLICATIONS

Search Report for GB0821122.9 searched Mar. 19, 2009 (2 pages).

(Continued)

*Primary Examiner* — John Goff
(74) *Attorney, Agent, or Firm* — Wong, Cabello, Lutsch, Rutherford & Brucculeri LLP.

(57) ABSTRACT

A process for the production of surface functionalised nanoparticles, such as the production of semiconductor quantum dot nanoparticles incorporating surface-bound functional groups that increase the ease with which the dots can be employed in applications, such as incorporation into solvents, inks, polymers, glasses, metals, electronic materials and devices, bio-molecules and cells. Embodiments of the method include reacting first and second nanoparticle precursor species in the presence of a nanoparticle surface binding ligand X—Y—Z where X is a nanoparticle surface binding group, Y is a linker group, and Z is a functional group, in which Y comprises a polyethyleneglycol group and/or Z comprises an aliphatic group incorporating a terminal unsaturated group, the reaction being effected under conditions permitting binding of said surface binding ligand to the growing nanoparticles to produce said surface functionalised nanoparticles.

22 Claims, 5 Drawing Sheets

(56) References Cited

U.S. PATENT DOCUMENTS

| | | |
|---|---|---|
| 6,261,779 B1 | 7/2001 | Barbera-Guillem et al. |
| 6,322,901 B1 | 11/2001 | Bawendi et al. |
| 6,326,144 B1 | 12/2001 | Bawendi et al. |
| 6,333,110 B1 | 12/2001 | Barbera-Guillem |
| 6,379,635 B2 | 4/2002 | O'Brien et al. |
| 6,423,551 B1 | 7/2002 | Weiss et al. |
| 6,426,513 B1 | 7/2002 | Bawendi et al. |
| 6,607,829 B1 | 8/2003 | Bawendi et al. |
| 6,660,379 B1 | 12/2003 | Lakowicz et al. |
| 6,699,723 B1 | 3/2004 | Weiss et al. |
| 6,815,064 B2 | 11/2004 | Treadway et al. |
| 6,855,551 B2 | 2/2005 | Bawendi et al. |
| 6,914,264 B2 | 7/2005 | Chen et al. |
| 6,992,202 B1 | 1/2006 | Banger et al. |
| 7,041,362 B2 | 5/2006 | Barbera-Guillem |
| 7,151,047 B2 | 12/2006 | Chan et al. |
| 7,235,361 B2 | 6/2007 | Bawendi et al. |
| 7,264,527 B2 | 9/2007 | Bawendi et al. |
| 7,544,725 B2 | 6/2009 | Pickett et al. |
| 7,588,828 B2 | 9/2009 | Mushtaq et al. |
| 7,674,844 B2 | 3/2010 | Pickett et al. |
| 7,803,423 B2 | 9/2010 | O'Brien et al. |
| 7,867,556 B2 | 1/2011 | Pickett |
| 7,867,557 B2 | 1/2011 | Pickett et al. |
| 2003/0017264 A1 | 1/2003 | Treadway et al. |
| 2003/0106488 A1 | 6/2003 | Huang et al. |
| 2003/0148024 A1 | 8/2003 | Kodas et al. |
| 2004/0007169 A1 | 1/2004 | Ohtsu et al. |
| 2004/0036130 A1 | 2/2004 | Lee et al. |
| 2004/0110002 A1 | 6/2004 | Kim et al. |
| 2004/0110347 A1 | 6/2004 | Yamashita |
| 2004/0178390 A1 | 9/2004 | Whiteford et al. |
| 2004/0250745 A1 | 12/2004 | Ogura et al. |
| 2005/0098204 A1 | 5/2005 | Roscheisen et al. |
| 2005/0129947 A1 | 6/2005 | Peng et al. |
| 2005/0145753 A1 | 7/2005 | Sato et al. |
| 2006/0019098 A1 | 1/2006 | Chan et al. |
| 2006/0057382 A1 | 3/2006 | Treadway et al. |
| 2006/0061017 A1 | 3/2006 | Strouse et al. |
| 2006/0068154 A1 | 3/2006 | Parce et al. |
| 2006/0110279 A1 | 5/2006 | Han et al. |
| 2006/0118757 A1 | 6/2006 | Klimov et al. |
| 2006/0130741 A1 | 6/2006 | Peng et al. |
| 2007/0012941 A1 | 1/2007 | Cheon |
| 2007/0034833 A1 | 2/2007 | Parce et al. |
| 2007/0059705 A1 | 3/2007 | Lu et al. |
| 2007/0104865 A1 | 5/2007 | Pickett |
| 2007/0110816 A1 | 5/2007 | Jun et al. |
| 2007/0114520 A1 | 5/2007 | Garditz et al. |
| 2007/0125983 A1 | 6/2007 | Treadway et al. |
| 2007/0131905 A1 | 6/2007 | Sato et al. |
| 2007/0199109 A1 | 8/2007 | Yi et al. |
| 2007/0202333 A1 | 8/2007 | O'Brien et al. |
| 2007/0238126 A1 | 10/2007 | Pickett et al. |
| 2008/0107911 A1 | 5/2008 | Liu et al. |
| 2008/0112877 A1 | 5/2008 | Xiao et al. |
| 2008/0121844 A1 | 5/2008 | Jang et al. |
| 2008/0160306 A1 | 7/2008 | Mushtaq et al. |
| 2008/0220593 A1 | 9/2008 | Pickett et al. |
| 2008/0257201 A1 | 10/2008 | Harris et al. |
| 2008/0264479 A1 | 10/2008 | Harris et al. |
| 2009/0139574 A1 | 6/2009 | Pickett et al. |
| 2009/0212258 A1 | 8/2009 | McCairn et al. |
| 2009/0263816 A1 | 10/2009 | Pickett et al. |
| 2010/0059721 A1 | 3/2010 | Pickett et al. |
| 2010/0113813 A1 | 5/2010 | Pickett et al. |
| 2010/0123155 A1 | 5/2010 | Pickett et al. |
| 2010/0193767 A1 | 8/2010 | Naasani et al. |
| 2010/0212544 A1 | 8/2010 | Harris et al. |

FOREIGN PATENT DOCUMENTS

| | | |
|---|---|---|
| EP | 1783137 | 5/2007 |
| EP | 1854792 | 11/2007 |
| GB | 2429838 A | 3/2007 |
| JP | 2002121549 A * | 4/2002 |
| JP | 2005139389 A | 6/2005 |
| WO | WO-9710175 | 3/1997 |
| WO | WO-0017642 | 3/2000 |
| WO | WO-0204527 | 1/2002 |
| WO | WO-0224623 | 3/2002 |
| WO | WO-0229140 | 4/2002 |
| WO | WO-03099708 | 12/2003 |
| WO | WO-2004008550 A2 | 1/2004 |
| WO | WO-2004033366 A1 | 4/2004 |
| WO | WO-2004065362 A2 | 8/2004 |
| WO | WO-2004066361 A2 | 8/2004 |
| WO | WO-2005021150 A2 | 3/2005 |
| WO | WO-2005106082 A1 | 11/2005 |
| WO | WO-2005123575 A1 | 12/2005 |
| WO | WO-2006001848 | 1/2006 |
| WO | WO-2006017125 A2 | 2/2006 |
| WO | WO-2006075974 A1 | 7/2006 |
| WO | WO-2006116337 A2 | 11/2006 |
| WO | WO-2006118543 A1 | 11/2006 |
| WO | WO-2006134599 A1 | 12/2006 |
| WO | WO-2007020416 A1 | 2/2007 |
| WO | WO-2007049052 A2 | 5/2007 |
| WO | WO-2007060591 A2 | 5/2007 |
| WO | WO-2007065039 A2 | 6/2007 |
| WO | WO-2007098378 | 8/2007 |
| WO | WO-2007102799 A2 | 9/2007 |
| WO | WO-2008013780 A2 | 1/2008 |
| WO | WO-2008054874 A2 | 5/2008 |
| WO | WO-2008133660 A2 | 11/2008 |
| WO | WO-2009016354 A1 | 2/2009 |
| WO | WO-2009040553 | 4/2009 |
| WO | WO-2009106810 A1 | 9/2009 |

OTHER PUBLICATIONS

Agger, J.R. et al., "Growth of Quantum-Confined Indium Phosphide inside MCM-41" *J. Phys. Chem. B* (1998) 102, p. 3345.

Aldana, J. et al. "Photochemical Instability of CdSe Nanocrystals Coated by Hydrophilic Thiols", J. Am. Chem. Soc. (2001), 123: 8844-8850.

Alivisatos, A.P. "Perspectives on the Physical Chemistry of Semiconductor Nanocrystals", J. Phys. Chem., (1996), 100, pp. 13226-13239.

Arici et al., "Hybrid Solar Cells Based on Inorganic Nanoclusters and Conjugated Polymers", Thin Solid Films 451-452 (2004) 612-618.

Barron, "Group III Materials: New Phases and Nono-particles with Applications in Electronics and Optoelectronics," Office of Naval Research Final Report (1999).

Battaglia et al., "Colloidal Two-dimensional Systems: CdSe Quantum Shells and Wells," Angew Chem. (2003) 115:5189.

Bawendi, M.G. The Quantum Mechanics of Larger Semiconductor Clusters ("Quantum Dots"), Annu. Rev. Phys. Chem. (1990), 42: 477-498.

Berry, C.R. "Structure and Optical Absorption of AgI Microcrystals", Phys. Rev. (1967) 161: 848-851.

Bunge, S.D. et al. "Growth and morphology of cadmium chalcogenides: the synthesis of nanorods, tetrapods, and spheres from CdO and $Cd(O_2CCH_3)_2$", J. Mater. Chem. (2003) 13: 1705-1709.

Castro et al., "Nanocrystalline Chalcopyrite Materials ($CuInS_2$ and $CuInSe_2$) via Low-Temperature Pyrolysis of Molecular Single-Source Precursors", Chem. Mater. (2003) 15:3142-3147.

Castro et al., "Synthesis and Characterization of Colloidal CuInS2 Nanoparticles from a Molecular Single-Source Precursors," J. Phys. Chem. B (2004) 108:12429.

Chun et al., "Synthesis of $CuInGaSe_2$ Nanoparticles by Solvothermal Route", Thin Solid Films 480-481 (2005) 46-49.

Contreras et al., "$ZnO/ZnS(O,OH)/Cu(In,Ga)Se_2$/Mo Solar Cell with 18:6% Efficiency," from 3d World Conf. on Photovol. Energy Conv, Late News Paper, (2003) pp. 570-573.

Cui et al., "Harvest of near infrared light in PbSe nanocrystal-polymer hybrid photovoltaic cells," Appl. Physics Lett. 88 (2006) 183111-183111-3.

(56) References Cited

OTHER PUBLICATIONS

Cumberland et al., "Inorganic Clusters as Single-Source Precursors for Preparation of CdSe, ZnSe, and CdSe/ZnS Nanomaterials" *Chemistry of Materials*, 14, pp. 1576-1584, (2002).
Dabousi et al., "(CdSe)ZnS Core—Shell Quantum Dots: Synthesis and Characterization of a Size Series of Highly Luminescent Nanocrystallites," Jrl. Phys. Chem.,(1997) 101, pp. 9463-9475.
Dance et al., "Syntheses, Properties, and Molecular and Crystal Structures of $(Me_4N)_4[E_4M_{10}(SPh)_{16}]$ (E=S, Se; M=Zn, Cd): Molecular Supertetrahedral Fragments of the Cubic Metal Chalcogenide Lattice", J. Am. Chem. Soc. (1984) 106:6285.
Daniels et al., "New Zinc and Cadmium Chalcogenide Structured Nanoparticles," Mat. Res. Soc. Symp. Proc. 789 (2004).
Dehnen et al., "Chalcogen-Bridged Copper Clusters," Eur. J. Inorg. Chem., (2002) pp. 279-317.
Eisenmann et al., "New Phosphido-bridged Multinuclear Complexes of Ag and Zn," Zeitschrift fur anorganische und allgemeine Chemi (1995). (1 page—abstract).
Eychmüller, A. et al. "A quantum dot quantum well: CdS/HgS/CdS", *Chem. Phys. Lett.* 208, pp. 59-62 (1993).
Fendler, J.H. et al. "The Colloid Chemical Approach to Nanostructured Materials", Adv. Mater. (1995) 7:607-632.
Gao, M. et al. "Synthesis of PbS Nanoparticles in Polymer Matrices", J. Chem. Soc. Commun. (1994) pp. 2779-2780.
Gou et al., "Shape-Controlled Synthesis of Ternary Chalcogenide $ZnIn_2S_4$ and $CuIn(S,Se)_2$ Nano-/Microstructures via Facile Solution Route", J. Am. Chem. Soc. (2006) 128:7222-7229.
Gur et al., "Air stable all-inorganic nanocrystal solar cells processed from solution," *Lawrence Berkeley Natl. Lab., Univ. of California*, paper LBNL-58424 (2005).
Gurin, "Nanoparticles of Ternary Semiconductors in Colloids Low-Temperature Formation and Quantum Size Effects", Colloids Surf. A (1998) 142:35-40.
Guzelian, A. et al. "Colloidal chemical synthesis and characterization of InAs nanocrystal quantum dots", Appl. Phys. Lett. (1996) 69: 1432-1434.
Guzelian, A. et al., "Synthesis of Size-Selected, Surface-Passivated InP Nanocrystals", *J. Phys. Chem.* (1996) 100:7212.
Hagfeldt, A. et al. "Light-induced Redox Reactions in Nanocrystalline Systems", Chem. Rev. , (1995) 95:49-68.
Henglein, A. "Small-Particle Research: Physicochemical Properties of Extremely Small Colloidal Metal and Semiconductor Particles", Chem Rev. (1989) 89: 1861-1873.
Hirpo et al., "Synthesis of Mixed Copper-Indium Chalcogenolates. Single-Source Precursors for the Photovoltaic Materials CuInQ2 (Q = S, Se)," J. Am. Chem. Soc. (1993) 115:1597.
Hu et al., "Hydrothermal Preparation of $CuGaS_2$ Crystallites with Different Morphologies", Sol. State Comm. (2002) 121:493-496.
International Search Report for PCT/GB2005/001611 mailed Sep. 8, 2005 (5 pages).
Jegier, J.A. et al. "Poly(imidogallane): Synthesis of a Crystalline 2-D Network Solid and Its Pyrolysis to Form Nanocrystalline Gallium Nitride in Supercritical Ammonia", Chem. Mater. (1998) 10: 2041-2043.
Jiang et al., "Elemental Solvothermal Reaction to Produce Ternary Semiconductor $CuInE_2$ (E=S, Se) Nnaorods", Inorg. Chem. (2000) 39:2964-2965.
Kaelin et al., "CIS and CIGS layers from selenized nanoparticle precursors," Thin Solid Films 431-432 (2003) pp. 58-62.
Kapur et al., "Non-Vacuum processing of $CuIn_{1-x}GaxSe_2$ solar cells on rigid and flexible substrates using nanoparticle precursor inks," Thin Solid Films 431-432 (2003) pp. 53-57.
Kher, S. et al. "A Straightforward, New Method for the Synthesis of Nanocrystalline GaAs and GaP", Chem. Mater. (1994) 6: 2056-2062.
Kim et al., "Synthesis of $CuInGaSe_2$ Nanoparticles by Low Temperature Colloidal Route", J. Mech. Sci. Tech. (2005) 19:2085-2090.
Law et al., "Nanowire dye-sensitized solar cells," Nature Mater. (2005) vol. 4 pp. 455-459.

Li et al., "Synthesis by a Solvothermal Route and Characterization of $CuInSe_2$ Nanowhiskers and Nanoparticles", Adv. Mat. (1999) 11:1456-1459.
Lieber, C. et al. "Understanding and Manipulating Inorganic Materials with Scanning Probe Microscopes", *Angew. Chem. Int. Ed. Engl.* (1996) 35: 687-704.
Little et al., "Formation of Quantum-dot quantum-well heteronanostructures with large lattice mismatch: Zn/CdS/ZnS," 114 J. Chem. Phys. 4 (2001).
Lover, T. et al. "Preparation of a novel CdS nanocluster material from a thiophenolate-capped CdS cluster by chemical removal of SPh ligands", *J. Mater. Chem.* (1997) 7(4): 647-651.
Lu et al., "Synthesis of Nanocrystalline $CuMS_2$ (M=In or Ga) Through a Solvothermal Process", Inorg. Chem. (2000) 39:1606-1607.
Malik et al., "A Novel Route for the Preparation of CuSe and $CuInSe_2$ Nanoparticles", Adv. Mat., (1999) 11:1441-1444.
Matijevic, E. "Production of Mondispersed Colloidal Particles", Ann. Rev. Mater. Sci. (1985) 15: 483-518.
Matijevic, E., "Monodispersed Colloids: Art and Science", Langmuir (1986) 2:12-20.
Mekis, I. et al., "One-Pot Synthesis of Highly Luminescent CdSe/CdS Core-Shell Nanocrystals via Organometallic and "Greener" Chemical Approaches", *J. Phys. Chem. B.* (2003) 107: 7454-7462.
Mews et al., "Preparation, Characterization, and Photophysics of the Quantum Dot Quantum Well System CdS/HgS/CdS", J. Phys. Chem. (1994) 98:934.
Mićić et al., "Synthesis and Characterization of InP, GaP, and $GaInP_2$ Quantum Dots", *J. Phys. Chem.* (1995) pp. 7754-7759.
Milliron et al., "Electroactive Surfactant Designed to Mediate Electron Transfer between CdSe Nanocrystals and Organic Semiconductors," Adv. Materials (2003) 15, No. 1, pp. 58-61.
Murray, C.B. et al., "Synthesis and Characterization of Nearly Monodisperse CdE (E = S, Se, Te) Semiconductor Nanocrystallites", *J. Am. Chem. Soc.* (1993) 115 (19) pp. 8706-8715.
Müller et al., "From Giant Molecular Clusters and Precursors to Solid-state Structures," *Current Opinion in Solid State and Materials Science*, 4 (Apr. 1999) pp. 141-153.
Nairn et al., "Preparation of Ultrafine Chalcopyrite Nanoparticles via the Photochemical Decomposition of Molecular Single-Source Precursors", Nano Letters (2006) 6:1218-1223.
Nazeeruddin et al., "Conversion of Light to Electricity by *cis*-$X_2$Bis(2,2'-bipyridy1-4,4'-dicarboxylate)ruthenium(II) Charge-Transfer Sensitizers (X= Cl-, Br-, I-, CN-, and SCN-) on Nanocrystalline $TiO_2$ Electrodes," J. Am. Chem. Soc. (1993) 115:6382-6390.
Nazeeruddin et al., "Engineering of Efficient Panchromatic Sensitizers for Nanocrystalline $TiO_2$-Based Solar Cells," J. Am. Chem. Soc. (2001) 123:1613-1624.
O'Brien et al., "The Growth of Indium Selenide Thin Films from a Novel Asymmetric Dialkydiselenocarbamate," 3 Chem. Vap. Depos. 4, pp. 227 (1979).
Olshavsky, M.A., et al. "Organometallic Synthesis of GaAs Crystallites Exhibiting Quantum Confinement", J. Am. Chem. Soc. (1990) 112: 9438-9439.
Olson et al., "Effect of Polymer Processing on the Performance of Poly(3-hexylthiophene)/ZnO Nnaorod Photovoltaic Devices", J. Phys. Chem. C. (2007) 111:16640-16645.
Patent Act 1977 Search Report under Section 17 for Application No. GB0522027.2 dated Jan. 27, 2006 (1 page).
Patent Act 1977 Search Report under Section 17 for Application No. GB0606845.6 dated Sep. 14, 2006.
Patent Act 1977 Search Report under Section 17 for Application No. GB0719073.9.
Patent Act 1977 Search Report under Section 17 for Application No. GB0719075.4.
Patent Act 1977 Search Report under Section 17 for Application No. GB0723539.3 dated Mar. 27, 2008 (1 page).
Patents Act 1977: Search Report under Section 17 for Application No. GB0409877.8 dated Oct. 7, 2004 (2 pages).
Peng et al., "Kinetics of I-VI and III-V Colloidal Semiconductor Nanocrystal Growth: "Focusing" os Size Distributions", J. Am. Chem. Soc., (1998) 129: 5343-5344.

(56) References Cited

OTHER PUBLICATIONS

Peng et al., "Mechanisms of the Shape Evolution of CdSe Nanocrystals", J. Am. Chem. Soc. (2001) 123:1389.
Peng et al., "Shape control of CdSe nanocrystals", *Nature*, (2000) vol. 404, No. 6773, pp. 59-61.
Pradhan, N. et al. "Single-Precursor, One-Pot Versatile Synthesis under near Ambient Conditions of Tunable, Single and Dual Band Flourescing Metal Sulfide Nanoparticles", J. Am. Chem. Soc. (2003) 125: 2050-2051.
Qi et al., "Efficient polymer-nanocrystal quantum-dot photodetectors," Appl. Physics Lett. 86 (2005) 093103-093103-3.
Qu, L. et al. "Alternative Routes toward High Quality CdSe Nanocrystals", Nano Lett. (2001) vol. 1, No. 6, pp. 333-337.
Robel et al., "Quantum Dot Solar Cells. Harvesting Light Energy with CdSe Nanocrystals Molecularly Linked to Mesoscopic $TiO_2$ Films," J. Am. Chem. Soc. (2006) 128: 2385-2393.
Salata, O.V. et al. "Uniform GaAs quantum dots in a polymer matrix", Appl. Phys. Letters (1994) 65(2): 189-191.
Sercel, P.C. et al. "Nanometer-scale GaAs clusters from organometallic percursors", Appl. Phys. Letters (1992) 61: 696-698.
Shulz et al., "Cu-In-Ga-Se Nanoparticle Colloids as Spray Deposition Precursors for $Cu(In,Ga)Se_2$ Solar Cell Materials", J. Elect. Mat. (1998) 27:433-437.
Steigerwald, M.L. et al. "Semiconductor Crystallites: A Class of Large Molecules", *Acc. Chem. Res.* (1990) 23: 183-188.
Stroscio, J.A. et al. "Atomic and Molecular Manipulation with the Scanning Tunneling Microscope", Science (1991), 254: 1319-1326.
Timoshkin, "Group 13 imido metallanes and their heavier analogs $[RMYR']_n$ (M=Al, Ga, In; Y=N, P, As, Sb)," Coordination Chemistry Reviews (2005).
Trinidade et al., "A Single Source Spproach to the Synthesis of CdSe Nanocrystallites", *Advanced Materials*, 1996 vol. 8, No. 2, pp. 161-163.
Vayssieres et al., "Highly Ordered $SnO_2$ Nanorod Arrays from Controlled Aqueous Growth," Angew. Chem. Int. Ed. (2004) 43: 3666-3670.
Vittal, "The chemistry of inorganic and organometallic compounds with adameantane-like structures," Polyhedron, vol. 15, No. 10, pp. 1585-1642 (1996).
Wang Y. et al. "PbS in polymers, From molecules to bulk solids", J. Chem. Phys. (1987) 87: 7315-7322.
Weller, H. "Colloidal Semiconductor Q-Particles: Chemistry in the Transition Region Between Solid State and Molecules", Angew. Chem. Int. Ed. Engl. (1993) 32: 41-53.
Weller, H. "Quantized Semiconductor Particles: A Novel State of Mater for Materials Science", Adv. Mater. (1993) 5: 88-95.
Wells, R.L. et al. "Synthesis of Nanocrystalline Indium Arsenide and Indium Phosphide from Indium(III) Halides and Tris (trimethylsilyl)pnicogens. Synthesis, Characterization, and Decomposition Behavior of $I3In-P(SiMe3)3$", Chem. Mater. (1995) 7: 793-800.
Xiao et al., "A Mild Solvothermal Route to Chalcopyrite Quaternary Semiconductor $CuIn(Se_xS_{1-x})_2$ Nanocrystallites", J. Mater. Chem. (2001) 11:1417-1420.
Yang et al., "Studies of Electrochemical Synthesis of Ultrathin ZnO Nanorod/Nanobelt Arrays on Zn Substrates in Alkaline Solutions of Amine-Alcohol Mixtures", Crystal Growth & Design (2007) 12:2562-2567.
Yu et al., "Polymer Photovoltaic Cells: Enhanced Efficiencies via a Network of Internal Donor-Acceptor Heterojunctions," 270 Science 5243 (1995), pp. 1789-1791.
Zhong et al, "Composition-Tunable $Zn_xCu_{1-x}Se$ Nanocrytals with High Luminescence and Stability", Jrl Amer. Chem. Soc. (2003).
Zhong et al., "A Facile Route to Synthesize Chalcopyrite $CuInSe2$ Nanocrystals in Non-Coordinating Solvent", Nanotechnology 18 (2007) 025602.
Trinidade et al., "Nanocrystalline Semiconductors: Synthesis, Properties, and Perspectives", Chemistry of Materials, (2001) vol. 13, No. 11, pp. 3843-3858.
Materials Research Society Symposium Proceedings *Quantum Dots, Nanoparticles and Nanowires*, 2004, ISSN: 0272-9172.
International Search Report for PCT/GB2006/003028 mailed Jan. 22, 2007 (5 pages).
Nielsch et al., "Uniform Nickel Deposition into Ordered Alumina Pores by Pulsed Electrodeposition", *Advanced Materials*, 2000 vol. 12, No. 8, pp. 582-586.
Huang et al., "Bio-Inspired Fabrication of Antireflection Nanostructures by Replicating Fly Eyes", *Nanotechnology* (2008) vol. 19.
International Search Report for PCT/GB2009/001928 mailed Dec. 8, 2009 (3 pages).
International Search Report for PCT/GB2009/002605 mailed Feb. 22, 2010 (3 pages).
Kim et al. "Engineering $InAsxP1-x/InP/ZnSe$ III-V Alloyed Core-Shell Quantum Dots for the Near-Infrared" JACS Articles published on web Jul. 8, 2005.
Rao et al. (2004) "The Chemistry of Nanomaterials: Synthesis, Properties and Applications" p. 443.
Search Report for GB0813273.0 searched Dec. 8, 2008 (1 page).
Search Report for GB0814458.6 searched Dec. 5, 2008 (1 page).
Search Report for GB0820101.4 searched Mar. 3, 2009 (1 page).
Xie et al. "Synthesis and Characterization of Highly Luminescent CdSe-Core CdS/Zn0.5Cd0.5S/ZnS Multishell Nanocrystals" JACS Articles published on web Apr. 29, 2005.
Foneberov et al., "Photoluminescence of tetrahedral quantum-dot quantum wells" Physica E, 26:63-66 (2005).
Cao, "Effect of Layer Thickness on the Luminescence Properties of ZnS/CdS/ZnS quantum dot quantum well", J. of Colloid and Interface Science 284:516-520 (2005).
Harrison et al. "Wet Chemical Synthesis on Spectroscopic Study of CdHgTe Nanocrystals with Strong Near-Infrared Luminescence" Mat. Sci and Eng.B69-70:355-360 (2000).
Sheng et al. "In-Situ Encapsulation of Quantum Dots into Polymer Microsphers", Langmuir 22(8):3782-3790 (2006).
W. Peter Wuelfing et al., "Supporting Information for Nanometer Gold Clusters Protected by Surface Bound Monolayers of Thiolated Poly (ethylene glycol) Polymer Electrolyte" Journal of the American Chemical Society (XP002529160).
International Search Report for PCT/GB2009/000510 mailed Jul. 6, 2010 (16 pages).
International Search Report for PCT/GB2008/003958 mailed Sep. 4, 2009 (3 pages).
Banger et al., "Ternary single-source precursors for polycrystalline thin-film solar cells" Applied Organometallic Chemistry, 16:617-627, XP002525473 Scheme 1 Chemical Synthesis (2002).
D Qi, M Fischbein, M Drndic, S. Selmic, "Efficient polymer-nanocrystal quantum-dot photodetectors", Appl. Phys. Lett., 2004, 84, 4295.
Shen et al., "Photoacoustic and photoelectrochemical characterization of CdSe-sensitized Ti02 electrodes composed of nanotubes and nanowires" Thin Solid Films, Elsevier-Sequoia S.A. Lausanne, CH vol. 499, No. 1-2, Mar. 21, 2006, pp. 299-305, XP005272241 ISSN: 0040-6090.
Smestad GP, et al., "A technique to compare polythiophene solid-state dye sensitized Ti02 solar cells to liquid junction devices" Solar Energy Materials and Solar Cells, Elsevier Science Publishers, Amsterdam, NL, vol. 76, No. 1, Feb. 15, 2003, pp. 85-105, XP004400821 ISSN: 0927-0248.
Chen et al., "Electrochemically synthesized CdS nanoparticle-modified Ti02 nanotube-array photoelectrodes: Preparation, characterization, and application to photoelectrochemical cells" Journal of Photochemistry and Photobiology, a: Chemistry, Elsevier Sequoia Lausanne, CH, vol. 177, No. 2-3, Jan. 25, 2006, pp. 177-184, XP005239590 ISSN: 1010-6030.
Wang, et al., "In situ polymerization of amphiphilic diacetylene for hole transport in solid state dye-sensitized solar cells" Organic Electronics, El Sevier, Amsterdam NL, vol. 7, No. 6, Nov. 18, 2006, pp. 546-550, XP005773063 ISSN: 1566-1199.
International Search Report and Written Opinion for PCT/GB2008/001457 mailed Aug. 21, 2008 (14 pages).

(56) References Cited

OTHER PUBLICATIONS

Richardson et al., "Chemical Engineering: Chemical and Biochemical Reactors and Process Control," vol. 3, Third Edition, pp. 3-5 (1994).

Borchert et al., "High Resolution Photoemission STudy of CdSe and CdSe/ZnS Core-Shell Nanocrystals," Journal of Chemical Physics, vol. 119, No. 3, pp. 1800-1807 (2003).

Gaponik et al., "Thiol-Capping of CdTe Nanocrystals: An Alternative to Organometallic Synthetic Routes," Journal of Physical Chemistry B, vol. 106, No. 29, pp. 7177-7185 (2002).

Pickett et al., "Syntheses of Semiconductor Nanoparticles Using Single-Molecular Precursors," The Chemical Record, vol. 1 pp. 467-479 (2001).

\* cited by examiner

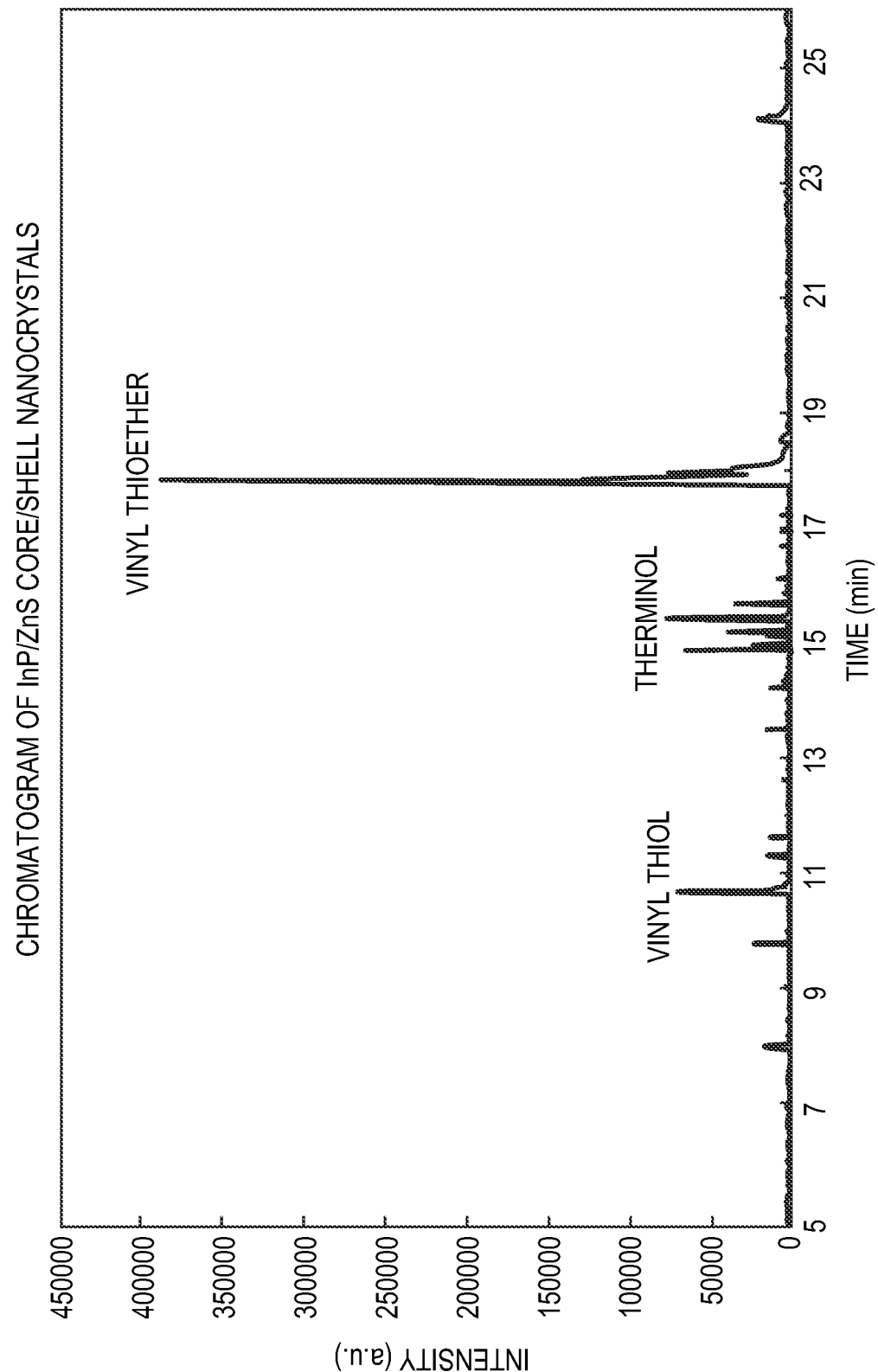

SURFACE FUNCTIONALISED NANOPARTICLES

RELATED APPLICATIONS

This application claims the benefit of and priority to co-pending U.S. Provisional Patent Application Ser. No. 61/088,100 filed Aug. 12, 2008, the entire content of which is hereby incorporated by reference. This application also claims the benefit of GB 0814458.6 filed Aug. 7, 2008, the entire content of which is hereby incorporated by reference.

FIELD OF THE INVENTION

The present invention relates to a process for the production of surface functionalised nanoparticles, particularly but not exclusively, the production of semiconductor quantum dot nanoparticles incorporating surface-bound functional groups that increase the ease with which the dots may be employed in applications, such as incorporation into solvents, inks, polymers, glasses, metals, electronic materials and devices, and bio-molecules and cells.

BACKGROUND

The size of a semiconductor nanoparticle generally dictates the electronic properties of the material, the band gap energy being inversely proportional to the size of the semiconductor nanoparticle as a consequence of quantum confinement effects. In addition, the large surface-area-to-volume ratio of the nanoparticle may have a profound impact upon the physical and chemical properties of the nanoparticle.

Two fundamental factors, both related to the size of the individual semiconductor nanoparticle, are primarily responsible for their unique properties. The first is the large surface-to-volume ratio: as a particle becomes smaller, the ratio of the number of surface atoms to those in the interior increases. This leads to the surface properties playing an important role in the overall properties of the material. The second factor is that, with many materials including semiconductor nanoparticles, the electronic properties of the material change with size. Moreover, because of quantum confinement effects, the band gap typically gradually becomes larger as the size of the particle decreases. This effect is a consequence of the confinement of an 'electron in a box' giving rise to discrete energy levels similar to those observed in atoms and molecules, rather than a continuous band as observed in the corresponding bulk semiconductor material. Thus, for a semiconductor nanoparticle, because of the physical parameters, the "electron and hole," produced by the absorption of electromagnetic radiation, a photon, with energy greater then the first excitonic transition, are closer together than in a corresponding macrocrystalline material. Moreover the Coulombic interaction cannot be neglected. This may lead to a narrow bandwidth emission that is dependent upon the particle size and composition of the nanoparticle material. Thus, quantum dots generally have higher kinetic energy than the corresponding macrocrystalline material and consequently the first excitonic transition (band gap) increases in energy with decreasing particle diameter.

Core semiconductor nanoparticles that consist of a single semiconductor material along with an outer organic passivating layer tend to have relatively low quantum efficiencies due to electron-hole recombination occurring at defects and dangling bonds situated on the nanoparticle surface that can lead to non-radiative electron-hole recombinations.

One method to eliminate defects and dangling bonds on the inorganic surface of the quantum dot is to grow a second inorganic material, having a wider band-gap and small lattice mismatch to that of the core material epitaxially on the surface of the core particle, to produce a "core-shell" particle. Core-shell particles separate any carriers confined in the core from surface states that would otherwise act as non-radiative recombination centres. One example is ZnS grown on the surface of CdSe cores.

Another approach is to prepare a core-multi shell structure where the "electron-hole" pair is completely confined to a single shell layer consisting of a few monolayers of a specific material such as a quantum dot-quantum well structure. Here, the core is of a wide band gap material, followed by a thin shell of narrower band gap material, and capped with a further wide band gap layer, such as CdS/HgS/CdS grown using substitution of Hg for Cd on the surface of the core nanocrystal to deposit just a few monolayers of HgS which is then overgrown by monolayers of CdS. The resulting structures exhibited clear confinement of photo-excited carriers in the HgS layer.

To add further stability to quantum dots and help to confine the electron-hole pair, one of the most common approaches is to epitaxially grow a compositionally graded alloy layer on the core. This can help to alleviate strain that could otherwise led to defects. Moreover, for a CdSe core, in order to improve structural stability and quantum yield, rather than growing a shell of ZnS directly on the core, a graded alloy layer of $Cd_{1-x}Zn_xSe_{1-y}S_y$ may be used. This has been found to enhance the photoluminescence emission of the quantum dots.

Doping quantum dots with atomic impurities is an efficient way also of manipulating the emission and absorption properties of the nanoparticle. Procedures for doping of wide band gap materials such as zinc selenide and zinc sulphide with manganese and copper (ZnSe:Mn or ZnS:Cu) have been developed. Doping with different luminescence activators in a semiconducting nanocrystal can tune the photoluminescence and electroluminescence at energies even lower than the band gap of the bulk material, whereas the quantum size effect can tune the excitation energy with the size of the nanocrystals without causing a significant change in the energy of the activator related emission.

The coordination about the final inorganic surface atoms in any core, core-shell or core-multi shell, doped or graded nanoparticle is incomplete, with highly reactive, non-fully coordinated atoms "dangling bonds" on the surface of the particle, which can lead to particle agglomeration. This problem may be overcome by passivating (also referred to as "capping") the "bare" surface atoms with protecting organic groups.

An outermost layer of organic material or sheath material (referred to as a "capping agent") helps to inhibit particle aggregation and protects the nanoparticles from their surrounding electronic and chemical environment. A schematic illustration of such a nanoparticle is provided in FIG. 1. In many cases, the capping agent is the solvent in which the nanoparticle preparation is undertaken, and includes a Lewis base compound or a Lewis base compound diluted in an inert solvent, such as a hydrocarbon. The lone pair of electrons on the Lewis base capping agent are capable of a donor-type coordination to the surface of the nanoparticles. Suitable Lewis base compounds include mono- or mulit-dentate ligands, such as phosphines (trioctylphosphine, triphenolphosphine, t-butylphosphine), phosphine oxides (trioctylphosphine oxide), alkyl phosphonic acids, alkyl-amines (hexadecylamine, octylamine), aryl-amines, pyridines, long chain fatty acids and thiophenes, but is not restricted to these materials.

The widespread exploitation of quantum dot nanoparticles has been restricted by their physical/chemical instability and incompatibility with many applications. Consequently, a series of surface modification procedures has been employed to render the quantum dots more stable and compatible with a desired application. This has been attempted mainly by making the capping agent bi- or multi functional or by overcoating the capping layer with an additional organic layer that has functional groups that can be used for further chemical linkage.

The most widely used quantum dot surface modification procedure is known as 'ligand exchange'. The ligand molecules that inadvertently coordinate to the surface of the quantum dot during the core synthesis and shelling procedure are subsequently exchanged with a ligand compound that introduces a desired property or functional group. Inherently, this ligand exchange strategy reduces the quantum yield of the quantum dots considerably. This process is illustrated schematically in FIG. 2.

An alternative surface modification strategy interchelates discrete molecules or polymer with the ligand molecules that are already coordinated to the surface of the quantum dot during the shelling procedure. These post synthesis interchelation strategies often preserve the quantum yield but may result in quantum dots of substantially larger size. This process is illustrated schematically in FIG. 3.

Current ligand exchange and interchelation procedures may render the quantum dot nanoparticles more compatible with their desired application but typically results in lower quantum yield due to damage to the inorganic surface of the quantum dots and/or an increase in the size of the final nanoparticles.

SUMMARY

Embodiments of the present invention may obviate or mitigate one or more of the problems described above.

Embodiments of the present invention generally relate to a method for producing surface functionalised nanoparticles by reacting first and second nanoparticle precursor species in the presence of a nanoparticle surface binding ligand incorporating a nanoparticle binding group and a functional group, the reaction being effected under conditions permitting binding of the surface binding ligand to the growing nanoparticles to produce the surface functionalised nanoparticles.

Some embodiments of the invention feature a method for producing surface functionalised nanoparticles. The method includes reacting first and second nanoparticle precursor species in the presence of a nanoparticle surface binding ligand having the formula X—Y—Z. X is a nanoparticle surface binding group, Y is a linker group, and Z is a functional group, in which Y includes a polyethyleneglycol group and/or Z includes an aliphatic group incorporating a terminal unsaturated group. The reaction may be effected under conditions permitting binding of the surface binding ligand to growing nanoparticles to produce the surface functionalised nanoparticles.

One or more of the following features may be included. The first nanoparticle precursor species may be contacted by the nanoparticle surface binding ligand so as to effect binding of the surface binding ligand to the first nanoparticle precursor species prior to reacting the first nanoparticle precursor species with the second nanoparticle precursor species.

The first nanoparticle precursor species may contain a first ion to be incorporated into the growing nanoparticles, and the second nanoparticle precursor species may, contain a second ion to be incorporated into the growing nanoparticles. The first ion may be selected from group 11, 12, 13, or 14 of the periodic table and the second ion may be selected from group 14, 15, or 16 of the periodic table.

The first and second nanoparticle precursor species may be reacted in the presence of a molecular cluster compound. The molecular cluster compound may contain third and fourth ions, at least one of the third and fourth ions being different from the first and second ions contained in the first and second nanoparticle precursor species respectively. The third ion and fourth ion may each be separately selected from group 11, 12, 13, 14, 15, and/or 16 of the periodic table. The molecular cluster compound may be contacted by the first nanoparticle precursor species prior to being contacted by the second nanoparticle precursor species.

During the reaction, the first nanoparticle precursor species may be added in one or more portions and the second nanoparticle precursor species may be added in one or more portions. The first nanoparticle precursor species may be added in two or more portions, and a temperature of a reaction mixture containing the first and second nanoparticle precursor species and the nanoparticle surface binding ligand may be increased between the addition of each portion of the first nanoparticle precursor species. The second nanoparticle precursor species may be added in two or more portions, and a temperature of a reaction mixture containing the first and second nanoparticle precursor species and the nanoparticle surface binding ligand may be increased between the addition of each portion of the second nanoparticle precursor species.

The first nanoparticle precursor species may be a core nanoparticle and the second nanoparticle precursor species may contain a first ion to form at least a part of a shell to be deposited on a surface of the core nanoparticle. Alternatively, the second nanoparticle precursor species may be a core nanoparticle and the first nanoparticle precursor species may contain a first ion to form at least part of a shell to be deposited on a surface of the core nanoparticle.

During the reaction, both the first and the second nanoparticle precursor species may be added in one or more portions. The first nanoparticle precursor species may be added in two or more portions, and a temperature of a reaction mixture containing the first and second nanoparticle precursor species and the nanoparticle surface binding ligand may be increased between the addition of each portion of the first nanoparticle precursor species.

The second nanoparticle precursor species may be added in two or more portions and a temperature of a reaction mixture containing the first and second nanoparticle precursor species and the nanoparticle surface binding ligand may be increased between the addition of each portion of the second nanoparticle precursor species.

The core nanoparticle and the nanoparticle precursor species may be reacted with a third nanoparticle precursor species containing a second ion to form at least a portion of the shell to be deposited on the surface of the core nanoparticle. During the reaction the third nanoparticle precursor species may be added in one or more portions. In some embodiments, the third nanoparticle precursor species may be added in two or more portions and a temperature of a reaction mixture containing the first, second and third nanoparticle precursor species and the nanoparticle surface binding ligand may be increased between the addition of each portion of the third precursor species.

The functional group of the surface binding ligand may be a charged or polar group, or a crosslinkable or polymerizable group. The functional group of the surface binding ligand may be, e.g., a hydroxide salt, alkoxide salt, carboxylate salt, ammonium salt, sulfonate salt, and/or phosphate salt.

The nanoparticle surface binding ligand may be a polymeric compound, e.g., a polyether. In some embodiments, the polymeric compound may include an alkoxide group and a carboxylate group.

The terminal unsaturated group may be a vinyl group.

X may include at least one carboxylic acid group or at least one thiol group. Y may include a straight or branched aliphatic group, or an aromatic group.

The nanoparticle surface binding ligand may be poly(oxyethylene glycol) monomethyl ether acetic acid with n=1 to 5000. In some embodiments, the nanoparticle surface binding ligand may be 10-Undecylenic acid and/or 11-mercapto-undecene.

The nanoparticle surface binding ligand may have a formula of

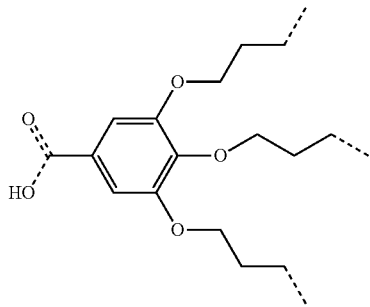

Some embodiments of the invention may feature a method for producing surface functionalised core semiconductor nanoparticles. The method may include reacting a first core nanoparticle precursor species containing a first ion to be incorporated into growing nanoparticles with a second core nanoparticle precursor species containing a second ion to be incorporated into the growing nanoparticles. The reaction may be effected in the presence of a nanoparticle surface binding ligand incorporating a nanoparticle binding group and a functional group, under conditions permitting binding of the surface binding ligand to the growing nanoparticles to produce the surface functionalised core semiconductor nanoparticles. The first and second core nanoparticle precursor species may be reacted in the presence of a molecular cluster compound.

Still other embodiments of the invention may feature a method for producing surface functionalised core-shell semiconductor nanoparticles. The method may include reacting a core semiconductor nanoparticle with a first nanoparticle precursor species containing a first ion to form at least a portion of a shell to be deposited on a surface of the core semiconductor nanoparticle, thereby growing a core-shell nanoparticle. The reaction may be effected in the presence of a nanoparticle surface binding ligand incorporating a nanoparticle binding group and a functional group, the reaction being effected under conditions permitting binding of the surface binding ligand to the surface of the growing core-shell semiconductor nanoparticles to produce the surface functionalised core-shell semiconductor nanoparticles.

One or more of the following features may be included. The core semiconductor nanoparticle may be contacted by the nanoparticle surface binding ligand so as to effect binding of the surface binding ligand to the core semiconductor nanoparticle prior to reacting the core semiconductor nanoparticle with the first nanoparticle precursor species. The first nanoparticle precursor species may be contacted by the nanoparticle surface binding ligand so as to effect binding of the surface binding ligand to the first nanoparticle precursor species prior to reacting the first nanoparticle precursor species with the core semiconductor nanoparticle.

The core semiconductor nanoparticle and the first nanoparticle precursor species may be reacted with a second nanoparticle precursor species containing a second ion to form at least a portion of the shell to be deposited on the surface of the core semiconductor nanoparticle.

A surface functionalised nanoparticle may be produced using any of the above methods, the surface functionalised nanoparticle including a nanoparticle bound to a nanoparticle surface binding ligand, the ligand incorporating a nanoparticle binding group and a functional group.

BRIEF DESCRIPTION OF DRAWINGS

Embodiments of the present invention are illustrated with reference to the following non-limiting examples and figures.

FIG. 8 is a chromatogram of InP/ZnS core/shell nanocrystals prepared in accordance with an embodiment of the present invention in Example 7.

DETAILED DESCRIPTION

Embodiments of the present invention generally relate to a method for producing surface functionalised nanoparticles including reacting first and second nanoparticle precursor species in the presence of a nanoparticle surface binding ligand incorporating a nanoparticle binding group and a functional group, the reaction being effected under conditions permitting binding of the surface binding ligand to the growing nanoparticles to produce the surface functionalised nanoparticles.

According to a first aspect of the present invention, a method is provided for producing surface functionalised nanoparticles including reacting first and second nanoparticle precursor species in the presence of a nanoparticle surface binding ligand having the formula

X—Y—Z where X is a nanoparticle surface binding group, Y is a linker group, and Z is a functional group, in which Y includes a polyethyleneglycol group and/or Z includes an aliphatic group incorporating a terminal unsaturated group, the reaction being effected under conditions permitting binding of the surface binding ligand to the growing nanoparticles to produce the surface functionalised nanoparticles.

Figure 1:
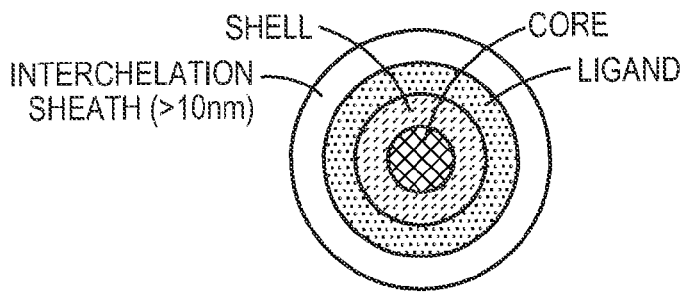
FIG. 1 is a schematic illustration of a prior art core-shell quantum dot nanoparticle incorporating an interchelated surface ligand.
Figure 2:
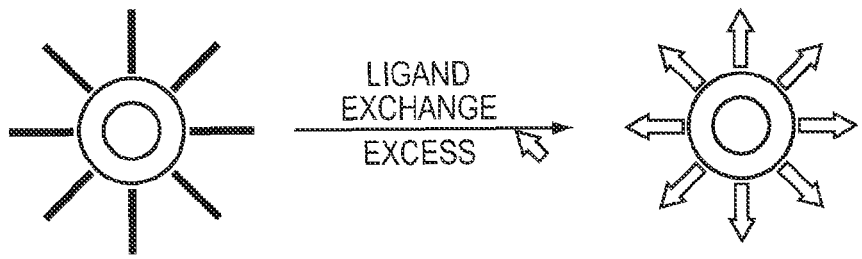
FIG. 2 is a schematic illustration of the prior art process of ligand exchange.
Figure 3:
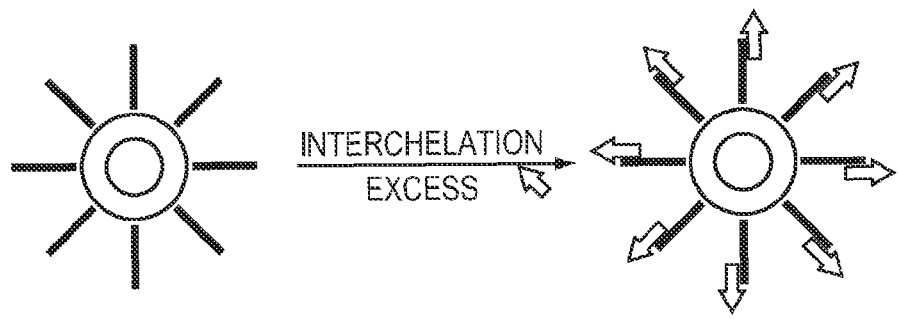
FIG. 3 is a schematic illustration of the prior art process of ligand interchelation.
Figure 4:
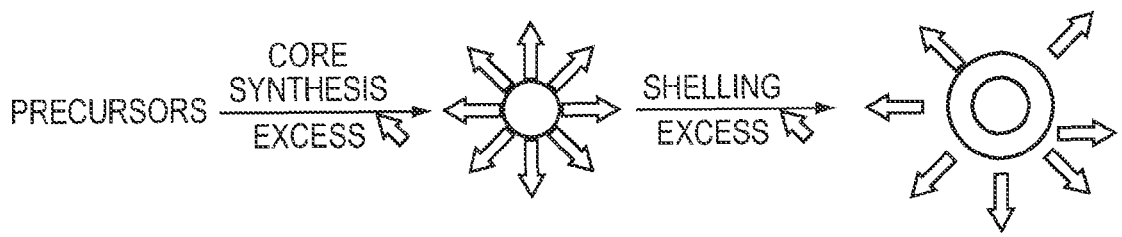
FIG. 4 is a schematic illustration of the process of an embodiment of the present invention to provide surface functionalised nanoparticles.

Embodiments of the present invention provide a method for converting nanoparticle precursor species to the material of the final nanoparticles whilst also providing a functionalised layer on the outer surface of the final nanoparticles. An exemplary embodiment of the method of the present invention is depicted schematically in FIG. 4. It has previously typically been necessary to carry out this process in at least two separate sequential steps, a first step involving production of the nanoparticles, and a separate second step involving either ligand exchange or interchelation to provide a functionalised ligand on the surface of the nanoparticles (see FIGS. 2 and 3). However, it has surprisingly been found that the nanoparticle precursor species can be combined in the presence of the functionalised nanoparticle surface binding ligand without harming the ability of the nanoparticle precursors to combine and react together, or the ability for the surface binding ligand to bind to the surface of the final nanoparticles.

It is still more surprising that the method of the first aspect of the present invention can be applied to the production of surface functionalised core nanoparticles from two or more sources of ions to be incorporated into the growing nanoparticles (optionally in the presence of a molecular cluster compound as described in the co-pending European patent application (publication No. EP1743054A) and UK patent application (application No. 0714865.3) both references hereby incorporated by reference in their entireties), as well as the production of surface functionalised core-shell nanoparticles where deposition of an outer shell layer can be carried out in the presence of a surface binding ligand.

Embodiments of the present invention thus provide a strategy for intentionally coordinating a chosen pre-chemically functionalised ligand to the surface of the quantum dot nanoparticle in-situ during core growth and/or shelling of nanoparticles. This strategy helps circumvent the need for post-nanoparticle synthesis surface modification procedures and thereby generates quantum dot nanoparticles in fewer manipulation steps that may be physically/chemically robust, have high quantum yield, have small diameter and are compatible with their intended application, which may include, but is not restricted to, incorporation of the nanoparticles into solvents, devices, inks, polymers, glasses, or attachment of the quantum dot nanoparticles, via chemical reaction to form a direct bond, to cells, biomolecules, metals, molecules or polymers.

Some embodiments of the invention facilitate synthesis of nanoparticles in a capping agent that has a nanoparticle binding group that may passivate the surface of the nanoparticle and an additional ligand that has the ability for further chemical linkage, such as cross linking about the nanoparticle or incorporation within polymeric materials.

The first and second precursor species and the surface binding ligand may be combined together in any desirable order, provided the first and second precursors react in the presence of the ligand. Preferably the first nanoparticle precursor species is contacted by the nanoparticle surface binding ligand so as to effect binding of the surface binding ligand to the first precursor species prior to reacting the first precursor species with the second nanoparticle precursor species.

Application of Method to Forming Nanoparticle Cores

In a first preferred embodiment of the method forming the first aspect of the present invention, the first nanoparticle precursor species contains a first ion to be incorporated into the growing nanoparticles and the second nanoparticle precursor species contains a second ion to be incorporated into the growing nanoparticles.

A second aspect of the present invention provides a method for producing surface functionalised core semiconductor nanoparticles, the method including reacting a first core nanoparticle precursor species containing a first ion to be incorporated into the growing nanoparticles with a second core nanoparticle precursor species containing a second ion to be incorporated into the growing nanoparticles, the reaction being effected in the presence of a nanoparticle surface binding ligand incorporating a nanoparticle binding group and a functional group, under conditions permitting binding of the surface binding ligand to the growing nanoparticles to produce the surface functionalised nanoparticles.

The nanoparticle surface binding ligand employed in the second aspect of the present invention may be in accordance with the ligand employed in accordance with the first aspect of the present invention. By way of example, in a preferred embodiment of the second aspect of the present invention the nanoparticle surface binding ligand has the formula having the formula X—Y—Z as set out above with respect to the first aspect of the present invention.

The first and second ions may be selected from any desirable group of the periodic table, such as but not limited to group 11, 12, 13, 14, 15, or 16 of the periodic table. The first and/or second ion may be a transition metal ion or a d-block metal ion. Preferably the first ion is selected from group 11, 12, 13, or 14 and the second ion is selected from group 14, 15, or 16 of the periodic table.

It is particularly preferred that the first and second (core) nanoparticle precursor species are reacted in the presence of a molecular cluster compound, as exemplified below in Example 1. The method may employ the methodology set out in the co-pending European patent application (publication No. EP1743054A). The molecular cluster compound may contain third and fourth ions. At least one of the third and fourth ions is preferably different to the first and second ions contained in the first and second (core) nanoparticle precursor species respectively. The third and fourth ions may be selected from any desirable group of the periodic table, such as but not limited to group 11, 12, 13, 14, 15, or 16 of the periodic table. The third and/or fourth ion may be a transition metal ion or a d-block metal ion. Preferably the third ion is selected from group 11, 12, 13, or 14 and the fourth ion is selected from group 14, 15, or 16 of the periodic table. By way of example, the molecular cluster compound may incorporate third and fourth ions from groups 12 and 16 of the periodic table respectively and the first and second ions derived from the first and second (core) nanoparticle precursor species may be taken from groups 13 and 15 of the periodic table respectively. Accordingly, the methods according to the first and second aspects of the present invention may employ methodology taken from the co-pending UK patent application (application No. 0714865.3).

The first and second (core) nanoparticle precursor species, molecular cluster compound and the surface binding ligand may be combined together in any desirable order. One of the first and second (core) precursor species may be contacted by the molecular cluster compound before or during reaction with the other of the first and second (core) precursor species. It is particularly preferred that the first (core) nanoparticle precursor species is initially contacted by the surface binding ligand to form a first mixture, which is then contacted by the molecular cluster compound to form a second mixture and the second mixture is then contacted by the second (core) nanoparticle precursor species.

It will be appreciated that during the reaction of the first and second (core) nanoparticle precursor species, the first (core) nanoparticle precursor species may be added in one or more portions and the second (core) nanoparticle precursor species may be added in one or more portions. The first (core) nanoparticle precursor species is preferably added in two or more portions. In this case, it is preferred that the temperature of a reaction mixture containing the first and second (core) nanoparticle precursor species and the nanoparticle surface binding ligand is increased between the addition of each portion of the first (core) precursor species. Additionally or alternatively, the second (core) nanoparticle precursor species may be added in two or more portions, whereupon the temperature of a reaction mixture containing the first and second (core) nanoparticle precursor species and the nanoparticle surface binding ligand may be increased between the addition of each portion of the second (core) precursor species.

Application of Method to Forming Nanoparticle Shells

In a second preferred embodiment of the first aspect of the present invention the first nanoparticle precursor species is a core nanoparticle and the second nanoparticle precursor species contains a first ion to form part of a shell to be deposited on the surface of the core nanoparticle.

In a third preferred embodiment of the first aspect of the present invention the second nanoparticle precursor species is a core nanoparticle and the first nanoparticle precursor species contains a first ion to form part of a shell to be deposited on the surface of the core nanoparticle.

The second and third preferred embodiments describe approaches, exemplified below in Examples 2 and 3, whereby the general methodology set out in the first aspect of the present invention can be employed to form an outer shell, or layer, of a material on the outside of a core nanoparticle, where the outer shell is provided with a chemical functionalised outer surface.

A third aspect of the present invention related to the second and third preferred embodiments of the first aspect of the present invention provides a method for producing surface functionalised core-shell semiconductor nanoparticles, the method including reacting a core semiconductor nanoparticle with a first nanoparticle precursor species containing a first ion to form part of a shell to be deposited on the surface of the core semiconductor nanoparticle, the reaction being effected in the presence of a nanoparticle surface binding ligand incorporating a nanoparticle binding group and a functional group, the reaction being effected under conditions permitting binding of the surface binding ligand to the surface of the growing core-shell semiconductor nanoparticles to produce the surface functionalised core-shell semiconductor nanoparticles.

The nanoparticle surface binding ligand employed in the third aspect of the present invention may be in accordance with the ligand employed in accordance with the first aspect of the present invention. By way of example, in a preferred embodiment of the third aspect of the present invention the nanoparticle surface binding ligand having the formula X—Y—Z as set out above with respect to the first aspect of the present invention.

With regard to the third aspect of the present invention the surface binding ligand may contact one of the core nanoparticle and the first precursor species before contacting the other, or may contact both simultaneously. Thus, in accordance with the method set out in Example 2 below, the core nanoparticle may be contacted by the binding ligand so as to effect binding of the ligand to the core nanoparticle prior to reacting the core nanoparticle with the first precursor species. Alternatively, in accordance with Example 3 below, the first precursor species may be contacted by the ligand so as to effect binding of the surface binding ligand to the first nanoparticle precursor species prior to reacting the first precursor species with the core nanoparticle. Preferably the method according to the third aspect of the present invention further includes reacting the core nanoparticle and the first precursor species with a second nanoparticle precursor species containing a second ion to form part of the shell to be deposited on the surface of the core semiconductor nanoparticle.

In the second and third embodiments of the first aspect of the present invention and the third aspect of the present invention, the core nanoparticle preferably contains first and second core ions that may be selected from any desirable group of the periodic table, such as, but not limited to group 11, 12, 13, 14, 15, or 16 of the periodic table. The core nanoparticle may contain a transition metal ion and/or a d-block metal ion. Preferably the core nanoparticle contains an ion selected from group 11, 12, 13 or 14 and an ion selected from group 14, 15, or 16 of the periodic table.

The first ion contained in the nanoparticle precursor species that is to form part of the nanoparticle shell may be selected from any desirable group of the periodic table, including but not limited to group 11, 12, 13, 14, 15, and/or 16 of the periodic table. Moreover, the first ion may be a transition metal ion or a d-block metal ion.

The nanoparticle precursor species and/or the core nanoparticle may be added in one or more portions as appropriate. Preferably, at least one of the precursor species and core nanoparticle is added in two or more portions during the reaction. The temperature of a reaction mixture containing the precursor species, the core nanoparticle and/or the nanoparticle surface binding ligand may be increased between the addition of each portion of the precursor species and core nanoparticles.

It is particularly preferred that the method according to the second and third embodiments of the first aspect of the present invention and the third aspect of the present invention further includes reacting the core nanoparticle and the precursor species with a third nanoparticle precursor species containing a second ion to form part of the shell to be deposited on the surface of the core nanoparticle. The second ion may also be selected from any desirable group of the periodic table, including but not limited to group 11, 12, 13, 14, 15, and/or 16 of the periodic table. Moreover, the second ion may be a transition metal ion or a d-block metal ion.

It is particularly preferred that the first and/or second ion contained in the nanoparticle precursor species is/are different to the first and second core ions. By way of example, the core-shell nanoparticle may include a core predominantly made from a III-V semiconductor material (e.g., InP) and a shell predominantly made from a II-VI semiconductor material (e.g., ZnS). In this case, the first and second core ions are preferably indium and phosphide ions, and the first and second ions derived from the nanoparticle precursor species are preferably zinc and sulfide ions. Suitable nanoparticle precursor species may be Zn(Ac) or the like and $(TMS)_3P$.

When a third nanoparticle precursor species is being added to the reaction mixture including the surface binding ligand, the third nanoparticle precursor species may be added in one or more portions. The third nanoparticle precursor species is preferably added in two or more portions. In this case, it is preferred that the temperature of a reaction mixture containing the core nanoparticles, precursor species and the nanoparticle surface binding ligand is increased between the addition of each portion of the third precursor species.

Suitable Solvents for use in the Method of the Present Invention

The reaction between the nanoparticle precursors (and core nanoparticles where appropriate) may be carried out in any appropriate solvent. The reaction is preferably carried out in a solvent that is different from the nanoparticle surface binding ligand, although it will be appreciated that this does not have to be the case, and that in alternative embodiments the surface binding ligand may represent the solvent or one of the solvents in which the reaction is being conducted. The solvent may be a co-ordinating solvent (i.e., a solvent that co-ordinates the growing nanoparticles) or a non-co-ordinating solvent (i.e., a solvent that does not co-ordinate the growing nanoparticles). Preferably the solvent is a Lewis base compound, such as HDA, TOP, TOPO, DBS, octanol, and the like.

The Nanoparticle Surface Binding Ligand

The nanoparticle binding group of the surface binding ligand is preferably different to the functional group of the surface binding ligand. The functional group may or may not incorporate a protecting group chosen so as to be selectively removable during and/or after nanoparticle growth.

The nature of the functional group of the surface binding ligand may be chosen to bestow any desirable chemical or physical property to the final surface functionalised nanoparticles. For example, a ligand may be chosen that contains a functional group that bestows the surface functionalised nanoparticles with a predetermined reactivity towards a particular reagent. Alternatively, a ligand may be chosen that incorporates a functional group that bestows aqueous compatibility (i.e., the ability to be stably dispersed or dissolved in aqueous media) to the surface functionalised nanoparticles. Moreover, a functional group may provide the ability to cross-link surface binding ligands around the surface of the same nanoparticle, ligands bound to adjacent nanoparticles and/or other surrounding materials (e.g., polymers) that incorporate compatible cross-linkable groups.

Such a functional group may contain a single vinyl group, or more preferably two, three or more vinyl groups to facilitate cross-linking between the vinyl groups bound to the nanoparticles and/or between vinyl groups bound to the nanoparticles and vinyl groups contained in surrounding materials.

The functional group of the surface binding ligand may contain one or more atoms such as sulfur, nitrogen, oxygen, and/or phosphorous. The functional group may be, e.g., hydroxide, alkoxide, carboxylic acid, carboxylate ester, amine, nitro, polyethyleneglycol, sulfonic acid, sulfonate ester, phosphoric acid, and/or phosphate ester. Moreover, the functional group may be a charged or polar group, such as but not limited to a hydroxide salt, alkoxide salt, carboxylate salt, ammonium salt, sulfonate salt, and/or phosphate salt.

The surface binding ligand may contain any appropriate nanoparticle binding group to bind to the growing nanoparticles, i.e., the core nanoparticles being grown according to the first preferred embodiment or the shell being grown on the core nanoparticles according to the second/third preferred embodiments. Preferably the nanoparticle binding group contains an atom such as sulfur, nitrogen, oxygen, and/or phosphorous. The nanoparticle binding group may contain a species such as a thio group, an amino group, an oxo group, and/or a phospho group. The nanoparticle binding group may be, e.g., hydroxide, alkoxide, carboxylic acid, carboxylate ester, amine, nitro, polyethyleneglycol, sulfonic acid, sulfonate ester, phosphoric acid, and/or phosphate ester. Moreover, the nanoparticle binding group may be a charged or polar group, such as but not limited to a hydroxide salt, alkoxide salt, carboxylate salt, ammonium salt, sulfonate salt, or phosphate salt.

The binding group and the functional group of the surface binding ligand are preferably connected via a linker, which may take any desirable form. It is particularly preferred that the linker is, e.g., a covalent bond; a carbon, nitrogen, oxygen or sulfur atom; a substituted or unsubstituted, saturated or unsaturated aliphatic or alicyclic group; and/or a substituted or unsubstituted aromatic group.

The nanoparticle surface binding ligand may be a polymeric compound, such as a polyether, optionally including an alkoxide group and a carboxylate group. Preferably the ligand is a polyether with a terminal alkoxide group and a carboxylate group bonded to the opposite terminus. Particularly preferred ligands include polyethylene glycols and derivatives thereof in which at least one, more preferably both, of the terminal hydroxide groups of polyethylene glycol has been derivatised to provide alternative functional groups, such as an alkoxide group and/or a carboxylate group.

Embodiments of the present invention include methods for producing surface functionalised nanoparticles that are physically/chemically robust, have high quantum yield, have small diameter and are compatible with their intended application. Nanoparticles produced according to the present invention may be represented by Formula 1 below:

$$\text{QD-X—Y—Z} \qquad \text{Formula 1}$$

where QD represents a core or core-(multi)shell nanoparticle; and X—Y—Z represents the nanoparticle surface binding ligand in which X is a nanoparticle surface binding group; Y is a linker group linking X and Z; and Z is a functional group.

X and/or Z may be substituted or unsubstituted alkyl, substituted or unsubstituted aryl, substituted or unsubstituted heterocyclic, substituted or unsubstituted polyethyleneglycol (examples of substituents include but are not limited to halogen, ether, amine, amide, ester, nitrile, isonitrile, aldehyde, carbonate, ketone, alcohol, carboxylic acid, azide, imine, enamine, anhydride, acid chloride, alkyne, thiol, sulfide, sulfone, sulfoxide, phosphine, phosphine oxide), or a crosslinkable/polymerisable group (examples include carboxylic acid, amine, vinyl, alkoxysilane, epoxide).

X and/or Z may be a charged or polar group, such as a hydroxide salt, alkoxide salt, carboxylate salt, ammonium salt, sulfonate salt or phosphate salt. X and/or Z may be, e.g., —$SR^1$ ($R^1$=H, alkyl, aryl); —$OR^2$ ($R^2$=H, alkyl, aryl); —$NR^3R^4$ ($R^3$ and/or $R^4$=H, alkyl, aryl); —$CO_2R^5$ ($R^5$=H, alkyl, aryl); —$P(=O)OR^6OR^7$ ($R^6$ and/or $R^7$=H, alkyl, aryl); —$OR^8$ where $R^8$ is hydrogen or an alkyl group that may be substituted or unsubstituted, and/or saturated or unsaturated; —$C(O)OR^9$ where $R^9$ is hydrogen, a substituted or unsubstituted, saturated or unsaturated aliphatic or alicyclic group, or a substituted or unsubstituted aromatic group; —$NR^{10}R^{11}$ where $R^{10}$ and $R^{11}$ are independently hydrogen, a substituted or unsubstituted, saturated or unsaturated aliphatic or alicyclic group, or a substituted or unsubstituted aromatic group, or $R^{10}$ and $R^{11}$ may be linked such that forms a nitrogen-containing heterocyclic ring of any desirable size, e.g., a five, six or seven-membered ring; —$N^+R^{12}R^{13}R^{14}$ where $R^{12}$, $R^{13}$ and $R^{14}$ are independently hydrogen, a substituted or unsubstituted, saturated or unsaturated aliphatic or alicyclic group, or a substituted or unsubstituted aromatic group; —$NO_2$; —$(OCH_2CH_2)_nOR^{15}$ where $R^{15}$ is hydrogen, a substituted or unsubstituted, saturated or unsaturated aliphatic or alicyclic group, or a substituted or unsubstituted aromatic group; —$NO_2$; $S(O)_2OR^{16}$ where $R^{16}$ is hydrogen, a substituted or unsubstituted, saturated or unsaturated aliphatic or alicyclic group, or a substituted or unsubstituted aromatic group; and/or —P(OR$^{17}$)(OR$^{18}$)O where R$^{17}$ and R$^{18}$ are independently hydrogen, a substituted or unsubstituted, saturated or unsaturated aliphatic or alicyclic group, or a substituted or unsubstituted aromatic group.

Z may incorporate any appropriate protecting group. By way of example, Z may contain an acid labile protecting group, such as t-butyl, benzylic, trityl, silyl, benzoyl, fluorenyl, acetal, ester, or ethers, e.g., methoxymethyl ether, 2-methoxy(ethoxy)methyl ether. Alternatively, Z may contain a nucleophillic-base labile protecting group, including a carboxylic ester, sulfonium salt, amide, imide, carbamate, N-sulfonamide, trichloroethoxymethyl ether, trichloroethylester, trichloroethoxycarbonyl, allylic-ether/amine/acetal/carbonate/ester/carbamate to protect a carboxylic acid, alcohol, thiol etc. Moreover, Z may incorporate a benzyl amine protecting group that may be deprotected to provide an amine group, or Z may contain a cyclic carbonate when it is ultimately desirable to deprotect Z to provide a diol for further reaction. Y may be a single bond, alkyl, aryl, heterocyclic, polyethyleneglycol, substituted or unsubstituted alkyl, substituted or unsubstituted aryl, substituted or unsubstituted heterocyclic, substituted or unsubstituted polyethyleneglycol, (examples of substituents include halogen, ether, amine, amide, ester, nitrile, isonitrile, aldehyde, carbonate, ketone, alcohol, carboxylic acid, azide, imine, enamine, anhydride, acid chloride, alkyne, thiol, sulfide, sulfone, sulfoxide, phosphine, phosphine oxide), a crosslinkable/polymerisable group (examples include carboxylic acid, amine, vinyl, alkoxysilane, epoxide), or a group represented by Formula 2 below:

Formula 2 where k, m and n are each independently any number from 0 to around 10,000.

In further preferred embodiments of the present invention, X may be an acid group or an ester group, such as a carboxylic acid group or derivative or salt thereof, such as a carboxylate ester or carboxylate salt. In alternative embodiments, X may be a sulfonic acid group, sulfonate ester or salt; a phosphoric acid group, phosphate ester or salt; or an amino group. Z preferably includes one or more alkyl group, each containing at least one unsaturated group. The or each carbon-to-carbon double or triple bond may be a terminal unsaturated group (i.e., include an atom at the end of a carbon chain) or may be provided within the carbon chain. Where Z includes one or more alkyl groups, the or each alkyl chain may carry any desirable substituent(s). The linker group, Y, connecting X and Z may take any convenient form. For example, Y may contain one or more aliphatic groups and/or an aromatic groups. The aliphatic group(s) may contain a straight carbon chain, a branched carbon chain, or may be alicyclic. Y may further include one or more ether groups. In particularly preferred embodiment, Y includes a phenyl group bound to at least one, more preferably two or three, unsaturated alkyl groups optionally via ether links. A particularly preferred nanoparticle surface binding ligand (Ligand 1) has the structure shown below, that can cross-link to other ligands and/or surrounding species (e.g., compatible polymers or polymerizable monomers) via the three vinyl groups.

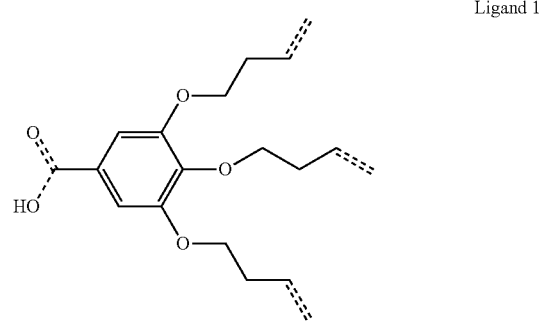

Ligand 1

Further preferred cross-linkable ligands of Formula 1 that may be used in embodiments of the method according to the present invention are shown below and incorporate a functional group, Z, which contains one or more vinyl groups bonded to an aliphatic or aromatic linker, Y, which is bonded to a nanoparticle binding ligand, X, of any desirable, structure, such as those described above. Preferred ligands incorporate one vinyl group, more preferably two vinyl groups, and most preferably three or more vinyl groups. Where Z contains two or more vinyl groups, then the vinyl groups may be bonded via respective alkyl groups to the same carbon atom, or to different carbon atoms (e.g., different carbon atoms of the same carbocyclic or heterocyclic ring, which may itself be saturated, partially saturated or aromatic). Nanoparticle binding group, X, may be monodentate or multidentate as described above. By way of example, X may incorporate one carboxylic acid group, as in Ligand 1, or X may incorporate two, three or more carboxylic acid groups. Where two or more carboxylic acid groups are present, each group may be bonded via an alkyl group to the same or different carbon atoms.

Exemplary monodentate aliphatic ligands include the following, where X is a carboxylic acid group, Z includes one, two or three vinyl groups, Y is a straight or branched aliphatic group, and each x is any integer (i.e., 0, 1, 2, 3 etc).

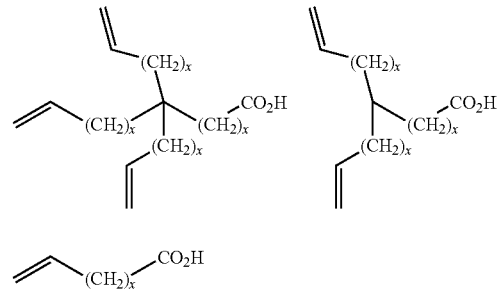

Exemplary monodentate aromatic ligands include the following, where X is a carboxylic acid group, Z includes one, two or three vinyl groups, Y contains an aromatic group, and each x is any integer (i.e., 0, 1, 2, 3, etc).

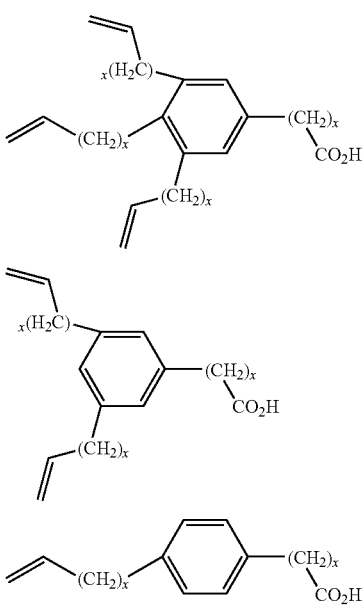

Exemplary bidentate aliphatic ligands include the following, where X contains two carboxylic acid groups, Z includes one, two or three vinyl groups, Y is a straight or branched aliphatic group, and each x is any integer (i.e., 0, 1, 2, 3, etc).

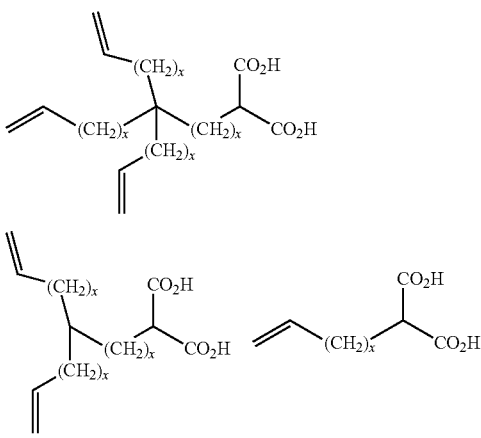

Exemplary tridentate aliphatic ligands include the following, where X contains three carboxylic acid groups, Z includes one, two or three vinyl groups, Y is a straight or branched aliphatic group, and each x is any integer (i.e., 0, 1, 2, 3, etc).

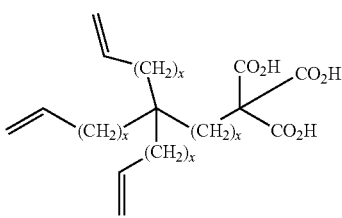

-continued

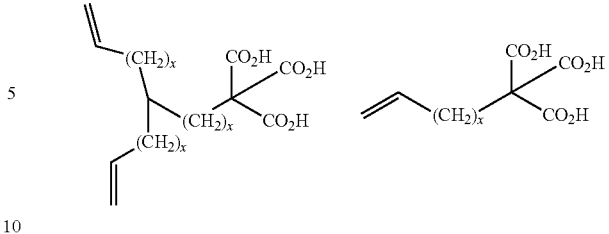

It will be appreciated that one or more of the carboxylic acid groups in any of the above exemplary structures may be replaced with an alternative nanoparticle binding group, such as, but not limited to, a carboxylic acid salt or ester, a sulfonic acid, ester or salt, a phosphoric acid, ester or salt, or an amino group. Moreover, linker group, Y, may contain groups other than the specific unsaturated aliphatic or aromatic groups shown above. For example, Y may incorporate one or more ether groups, carbon-to-carbon double bonds, and/or multicyclic aromatic or non-aromatic groups.

In a preferred embodiment, a method is provided according to the first aspect of the present invention, where the terminal unsaturated group is a vinyl group. That is, the nanoparticle surface binding ligand incorporates a carbon-to-carbon double bond at the end of the ligand furthest away from the nanoparticle surface.

In the formula X—Y—Z for a nanoparticle surface binding ligand in accordance to the first aspect of the present invention, it is preferred that X includes at least one carboxylic acid group or at least one thiol group. Preferably Y includes a straight or branched aliphatic group, or an aromatic group.

With regard to the first aspect of the present invention, the nanoparticle surface binding ligand may be poly(oxyethylene glycol)$_n$ monomethyl ether acetic acid where n=around 1 to around 5000. Preferably n is around 50 to 3000, more preferably around 250 to 2000, and most preferably around 350 to 1000. Alternatively, the nanoparticle surface binding ligand may be, e.g., 10-Undecylenic acid and/or 11-mercapto-undecene. As a further preferred alternative, the nanoparticle surface binding ligand is Ligand 1 as shown above.

Exemplary surface binding ligands according to Formula 1 that are used in the Examples below include poly(oxyethylene glycol)$_{350}$ monomethyl ether acetic acid, poly(oxyethylene glycol)$_{750}$ monomethyl ether acetic acid, poly(oxyethylene glycol)$_{2000}$ monomethyl ether acetic acid, 10-Undecylenic acid, Ligand 1 as shown above, and 11-mercapto-undecene.

Surface Functionalised Nanoparticles

A fourth aspect of the present invention provides surface functionalised nanoparticles produced using the method according to the first, second or third aspects of the present invention, the surface functionalised nanoparticle including a nanoparticle bound to a nanoparticle surface binding ligand, the ligand incorporating a nanoparticle binding group and a functional group.

Nanoparticles produced according to any of the aforementioned aspects of the present invention are preferably semiconductor nanoparticles, for example, core nanoparticles, core-shell nanoparticles, graded nanoparticles or core-multishell nanoparticles. The nanoparticles preferably includes one or more ions selected from any suitable group of the periodic table, such as but not limited to group 11, 12, 13, 14, 15, or 16 of the periodic table, transition metal ions and/or d-block metal ions. The nanoparticle core and/or shell (where applicable) may incorporate one or more semiconductor material such as, e.g., CdS, CdSe, CdTe, ZnS, ZnSe, ZnTe, InP, InAs, InSb, AlP, AlS, AlAs, AlSb, GaN, GaP, GaAs, GaSb, PbS, PbSe, Si, Ge, MgS, MgSe, MgTe, and combinations thereof.

Embodiments of the present invention relate to growing the final inorganic layer of a quantum dot nanoparticle in the same reaction as producing the first organic layer that has additional functionality, either immediately or after further chemical treatment of the organic layer if a protecting group has been used, whereby it has the ability to chemically link to other chemical entities.

The present invention describes a strategy that intentionally coordinates a chosen pre-chemically functionalised ligand to the surface of the quantum dot nanoparticle in-situ during core growth and/or shelling of the nanoparticles. This strategy circumvents the need for post synthesis surface modification procedures and generates quantum dot nanoparticles in fewer manipulation steps that are physically/chemically robust, have high quantum yield, have small diameter and are compatible with their intended application, which may include, but is not restricted to, incorporation of the nanoparticles into solvent, devices, inks, polymers, glasses or attachment of the quantum dot nanoparticles, via chemical reaction to form a direct bond, to cells, biomolecules, metals, molecules or polymers.

EXAMPLES

The following Examples describe methods for producing core semiconductor nanoparticles and depositing shells of semiconductor material on the cores using methods according to embodiments of the present invention.

Examples 1 and 4 describe the production of InP core nanoparticle quantum dots using a molecular cluster compound to seed nanoparticle growth according to the invention described in European patent publication EP1743054A. The cluster used in Examples 1 and 4 includes ions from groups 12 and 16 of the Periodic Table (Zn and S ions respectively) in accordance with the invention described in co-pending UK patent application No. 0714865.3.

Examples 2 and 3 describe methods for depositing a shell of ZnS on the InP core nanoparticles produced in Example 1, using a method according to an aspect of the present invention. Examples 5 and 6 describe methods for depositing shells of ZnS and ZnS/ZnO respectively on the InP core nanoparticles produced in Example 4, using a method according to an aspect of the present invention. Example 7 describes a method for preparing InP/ZnS core/shell nanoparticles in which the step of depositing the shell of ZnS on the InP core nanoparticles employs a method according to an aspect of the present invention.

Example 1

InP Quantum Dots Functionalised with Poly(oxyethylene glycol)$_{750}$ Monomethyl Ether Acetic Acid Dibutyl sebacate (100 ml) was added to a round bottom 3-neck flask (250 ml) and placed under high vacuum for 1 hour and 30 minutes at a temperature of 90° C. In a separate round bottom 3-neck flask (100 ml), dibutyl sebacate (45 ml) and indium acetate (5.036 g, 17.25 mmol) was placed under high vacuum at a temperature of 110° C.

Poly(oxyethylene glycol)$_{750}$ monomethyl ether acetic acid (51.76 mmol) was heated under high vacuum (~90° C.) for one hour in a reaction flask. After one hour, the reaction flask was allowed to cool before transferring the dibutyl sebacate and indium acetate mixture to the reaction flask under nitrogen. The reaction flask was then placed under high vacuum at 110° C. for a period of 16 hours to ensure any excess water present is removed. After 16 hours, a clear, pale yellow solution was formed.

Dibutyl sebacate (100 ml) was placed in a 3-neck round bottom flask (250 ml) and left to degas for 1 hour and 30 minutes at a temperature of 80° C. The temperature was then increased to 90° C. and $(Et_3NH)_4[Zn_{10}S_4(SPh)_{16}]$ cluster (0.47 g) added and allowed to stir for 30 minutes. After thirty minutes the temperature was increased to 100° C. and the following steps carried out. At 100° C. indium poly(oxyethylene glycol)$_{750}$ monomethyl ether acetate (0.25 M, 6 ml) was added dropwise. After the 6 ml addition, the reaction mixture was left to stir for 5 minutes, followed by the dropwise addition of $(TMS)_3P$ (0.25 M, 6 ml). the reaction temperature was increased to 150° C. and a second addition of In(PEG-OMe-750) (0.25 M, 8 ml) was made dropwise, left to stir for 5 minutes, followed by a second dropwise addition of $(TMS)_3P$ (0.25 M, 8 ml). The reaction mixture was increased to 180° C. Indium poly(oxyethylene glycol)$_{750}$ monomethyl ether acetate (0.25 M, 10 ml) was added dropwise, and after 5 minutes, $(TMS)_3P$ was added (0.25 M, 7 ml). The reaction temperature was increased to 200° C. and then annealed at 200° C. for 45 minutes after which the temperature was decreased to 160° C. and the reaction mixture left to anneal and stir vigorously for three days.

After the three day period the temperature was decreased to room temperature and the reaction mixture was isolated via the addition of acetonitrile until flocculation of the particles occurred. Once a precipitate had formed, the solvent was removed via cannula with the attachment of a filter. The remaining solid was redissolved into anhydrous chloroform (~94 ml) and syringed into a Schlenk tube under nitrogen.

Example 2

Forming a Shell of ZnS on InP Core Nanoparticles employing Poly(oxyethylene Glycol)$_{350}$ Monomethyl Ether Acetic Acid as Capping Agent In a 3-neck flask, di-n-butyl sebacate ester (11 ml) and poly(oxyethylene glycol)$_{350}$ monomethyl ether acetic acid (3.53 g, 7.618 mmol) were added and degassed at 50° C. for 15 minutes then cooled to room temperature. Indium phosphide quantum dots prepared according to Example 1 (3.3 ml, ~100 mg) were then added and degassed for a further 15 minutes. Anhydrous zinc acetate (0.71 g, 3.87 mmol) was added as a solid and the flask flushed several times with nitrogen. The solution was then heated to 180° C. for 5 hours to form a zinc rich quantum dot surface. $(TMS)_2S$ (1 M, 1 ml, 1 mmol) was added dropwise at 180° C. and the solution left for 30 minutes to complete the ZnS layer. The nanoparticles quantum dots incorporating a InP core with a ZnS shell were isolated and cleaned using diethylether and hexane (50:50).

Example 3

Forming a Shell of ZnS on InP Cores Employing Poly(oxyethylene Glycol)$_{2000}$ Monomethyl Ether Acetic Acid as Capping Agent Indium phosphide quantum dots prepared according to Example 1 (3.3 ml, ~100 mg) were transferred to a round bottomed flask and rotary evaporated to remove the chloroform. After the removal of chloroform the dots were dried under vacuum. In a 3-neck round bottom flask, dibutyl sebacate (10 ml), poly(oxyethylene glycol)$_{2000}$ monomethyl ether acetic acid ligand (17.07 g, 7.74 mmol) and zinc acetate (0.71 g, 3.87 mmol) were placed under vacuum at a temperature of 110° C. The dots and dibutyl sebacate (5 ml) were placed into a Schlenk tube and degassed for 15 minutes. After the poly (oxyethylene glycol)$_{2000}$ monomethyl ether acetic acid ligand and zinc acetate had dissolved to form a clear solution the temperature was decreased from 110° C. to 30° C. The dots in dibutyl sebacate were added to the poly(oxyethylene glycol)$_{2000}$ monomethyl ether acetic acid and zinc acetate reaction mixture and the temperature increased to 180° C. Octanethiol (0.175 mo, 1 mmol) was added dropwise then the solution was heated to 220° C. for 90 minutes to facilitate decomposition of the thiol to sulfide ions and complete the ZnS shell. The nanoparticle quantum dots incorporating an InP core with a ZnS shell were isolated and cleaned using diethylether and hexane (50:50).

Example 4

InP Quantum Dots Functionalised with 10-Undecylenic Acid

Dibutyl sebacate (100 ml) and 10-undecylenic acid (4.146 g) was added to a round bottom 3-neck flask (250 ml) and placed under high vacuum for 1 hour and 40 minutes at a temperature of 100° C. The temperature was reduced to 80° C., (Et$_3$NH)$_4$[Zn$_{10}$S$_4$(SPh)$_{16}$] cluster (0.47 g) was added and the solution placed under high vacuum for 30 minutes. After this time the temperature was increased to 100° C. and the following additions were made: at 100° C. triethyl indium (0.5 M in dibutyl sebacate, 3 ml) was added dropwise. After the 3 ml addition, the reaction mixture was left to stir for 5 minutes, followed by the dropwise addition of (TMS)$_3$P (0.5 M in dibutyl sebacate, 3 ml). The reaction temperature was increased to 160° C. and a second addition of triethyl indium (0.5 M, 0 ml) was made dropwise, left to stir for 5 minutes, followed by a second dropwise addition of (TMS)$_3$P (0.5 M, 4 ml). The reaction mixture was increased to 200° C. and annealed for 1 hour after which time the temperature was decreased to 150° C. and the reaction mixture left to anneal and stir vigorously for three days.

After the three-day period, the temperature was decreased to room temperature and the reaction mixture was isolated via the addition of acetonitrile (150 ml). Once the precipitate had formed, the solvent was removed by centrifugation. The remaining solid was re-dissolved into anhydrous chloroform and transferred into a conical flask. 10-Undeylenic acid (2 g) was added.

Post-Operative Treatment

HF—Acid Etching of InP Quantum Dots

A hydrofluoric acid solution was prepared by combining 8 ml aqueous hydrofluoric acid (58-62 wt % solution) and THF (32 ml).

HF stock solution was added portion-wise to the InP particles dispersed in chloroform. The reaction mixture was continuously irradiated with light from a 500 W halogen lamp passed through a 560 nm filter. After this the solvent was removed by evaporation. The residue was dispersed in chloroform, re-precipitated with acetonitrile and separated by centrifugation. The solid was dispersed into dibutyl sebacate.

Example 5

ZnS/ZnO Shelling of InP Employing 10-Undecylenic Acid as the Capping Agent

A flame dried three-necked flask (250 ml), equipped with a condenser with a side arm, a thermometer, a suba seal, and a stirrer bar was charged with dibutyl sebacate (15 ml) and 10-undecylenic acid (2.6 g) and degassed at 80° C. for 1 hour and 30 minutes. The flask was back filled with nitrogen and indium phosphide core particles produced according to Example 4 (1.3 g in 15 ml dibutyl sebacate) were added, the mixture degassed at 80° C. for 40 minutes, and then back filled with nitrogen.

Zinc acetate (1.4 g) was added, the mixture degassed at 80° C. for 30 minutes and backfilled with nitrogen three times. The reaction temperature was increased to 120° C. then 1-octanethiol (0.41 ml) was added dropwise. The temperature was then increased to 220° C. and held for 90 minutes. The temperature was decreased to 190° C., a further portion of 1-octanethiol (1.09 ml) was added and the temperature raised to 220° C. and held for 90 minutes. This completes the ZnS shell. The reaction solution was then cooled to 190° C. A ZnO layer was formed by the decomposition of the remaining zinc salt by the fast addition of 1-octanol (1.0 ml) and holding the temperature for 30 minutes. A further portion of 1-octanol (1.74 ml) was added to complete the ZnO layer and holding at the same temperature 30 minutes. The reaction mixture was then cooled to room temperature.

InP/ZnS/ZnO core-multishell nanoparticles, were isolated under N$_2$ with anhydrous acetonitrile and collected by centrifugation. The particles were dispersed in toluene and re-precipitated with anhydrous acetonitrile followed by centrifugation. The particles were re-dispersed in toluene followed by centrifugation. The supernatant was removed to a Schlenk tube.

The resulting core-multishell nanoparticles coated with 10-undecylenic acid as the capping agent may then be treated with a Hoveyda-Grubbs catalyst under standard conditions to cause the ligands to undergo acyclic diene polymerisation and/or ring closure metathesis and cross-link adjacent 10-undecylenic acid groups as shown in the exemplary reaction scheme below.

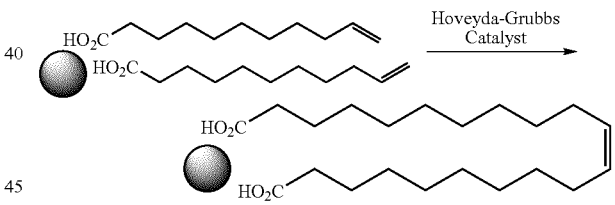

Example 6

Forming a Shell of ZnS on InP Cores Employing Ligand 1 as Capping Agent

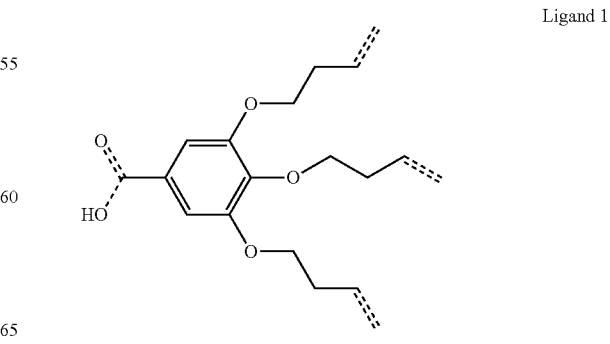

Ligand 1 was produced according to the reaction scheme shown below.

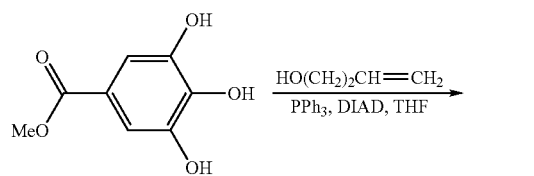

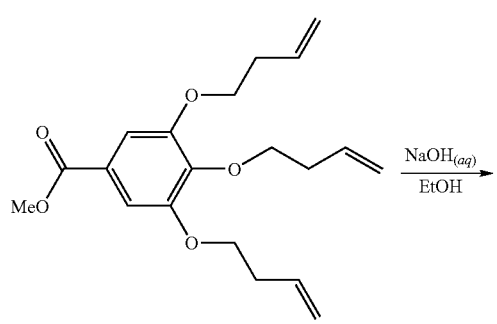

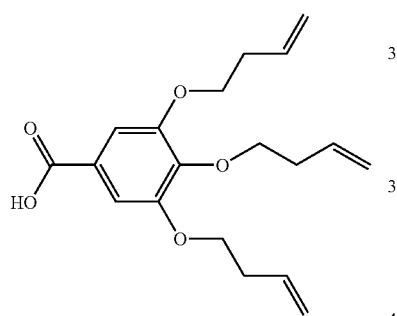

A flame dried three-necked flask (100 ml), equipped with a condenser with a side arm, a thermometer, a suba seal and a stirrer bar was charged with indium phosphide core nanoparticles (0.155 g in 4.4 ml dibutyl sebacate) and degassed at 100° C. for 1 hour. The flask was allowed to cool to room temperature and then back filled with nitrogen. Zinc acetate (0.7483 g) and Ligand 1 (0.5243 g) was then added, the mixture degassed at 55° C. for 1 hour and backfilled with nitrogen. The reaction temperature was increased to 190° C., tert-nonyl mercaptan (0.29 ml) was added dropwise, the temperature increased to 190° C. and held for 1 hour and 30 minutes. The temperature was decreased to 180° C., 1-octanol (0.39 ml) added and the temperature held for 30 minutes. The reaction mixture was cooled to room temperature.

InP/ZnS core-shell nanoparticles particles were isolated under $N_2$ in ethyl acetate by centrifugation. The particles were precipitated with acetonitrile followed by centrifugation.

The particles were dispersed in chloroform and re-precipitated with acetonitrile followed by centrifugation. This dispersion-precipitation procedure using chloroform and acetonitrile was repeated four times in total. The InP/ZnS core-shell particles were finally dispersed in chloroform.

The resulting core-multishell nanoparticles coated with Ligand 1 as the capping agent may then be treated with a Hoveyda-Grubbs catalyst under standard conditions to cross-link adjacent terminal vinyl groups as shown in the exemplary reaction scheme below.

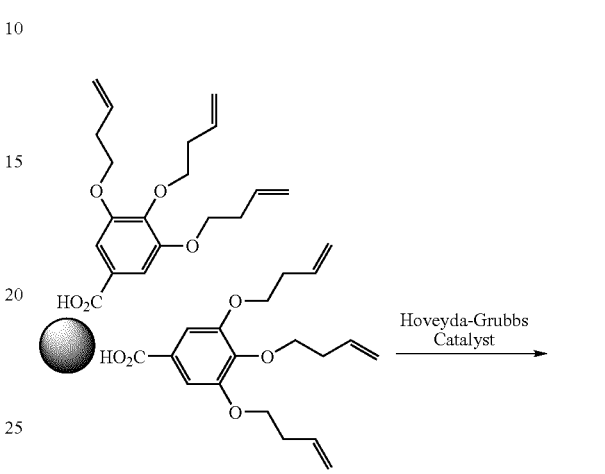

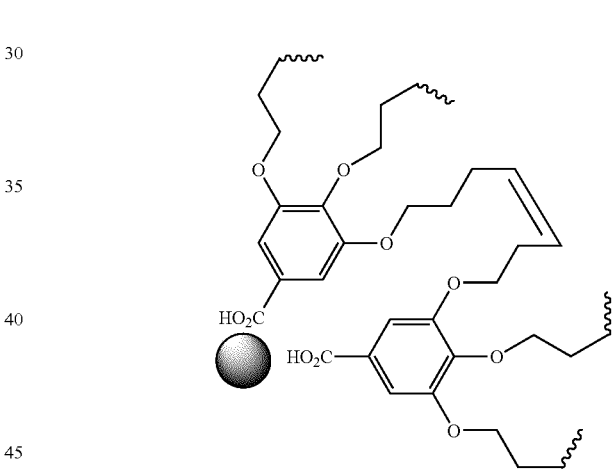

Alternatively, the terminal vinyl groups of Ligand 1 could be cross-linked before coordination to the nanoparticles as shown below.

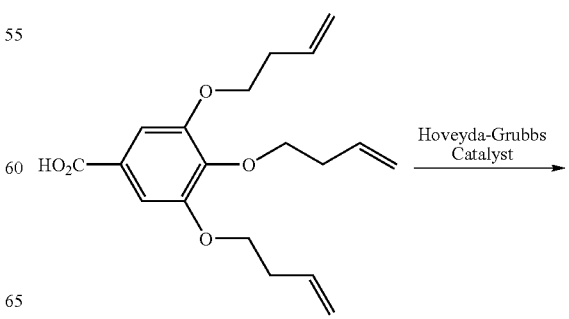

-continued

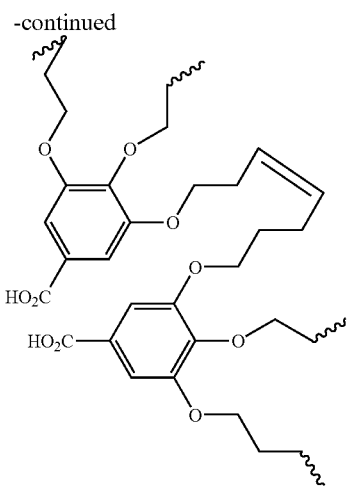

Example 7

Synthesis of InP Cores

Figure 5:
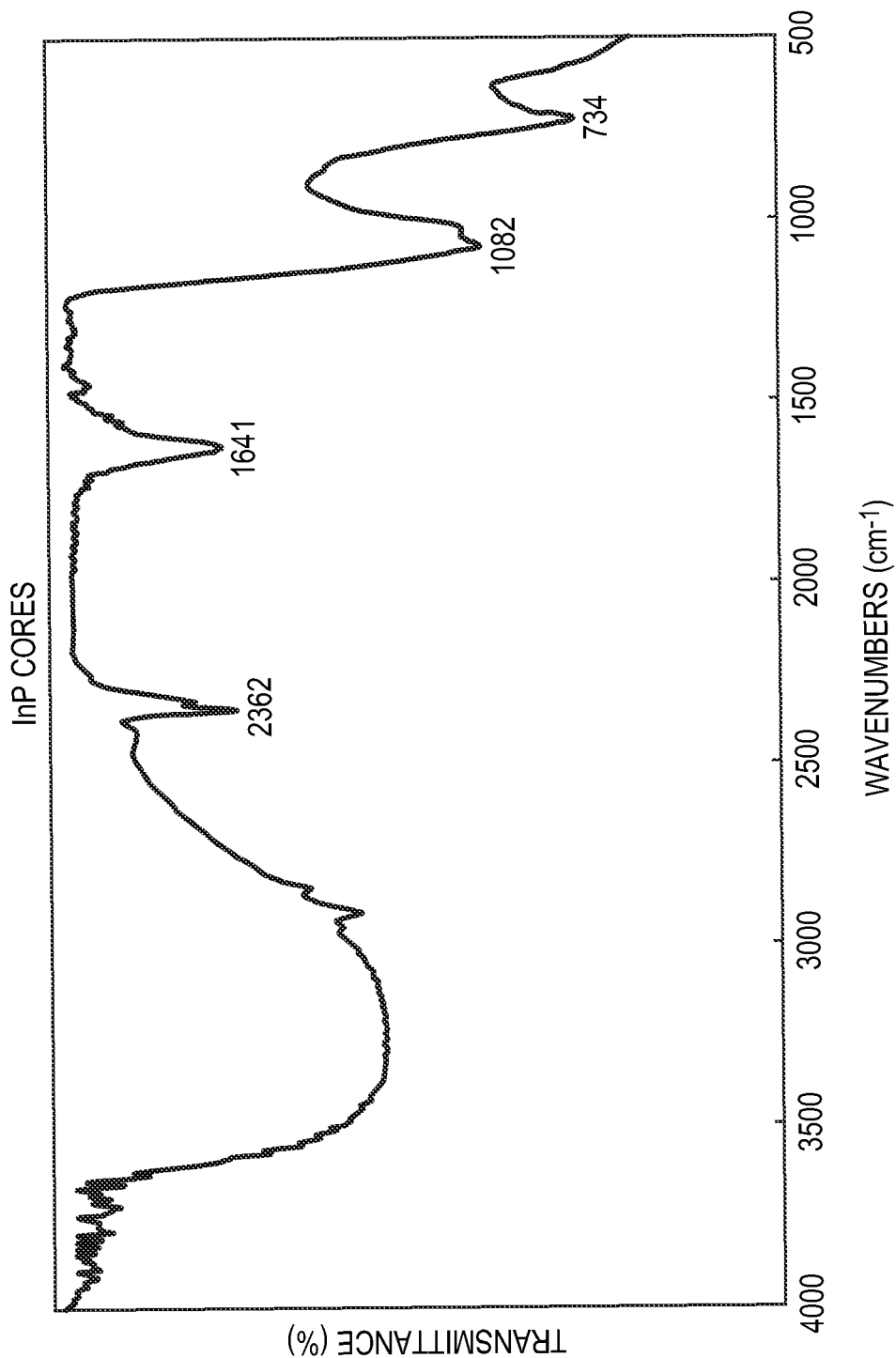
FIG. 5 is an IR spectrum of InP core nanocrystals prepared in Example 7.
Figure 6:
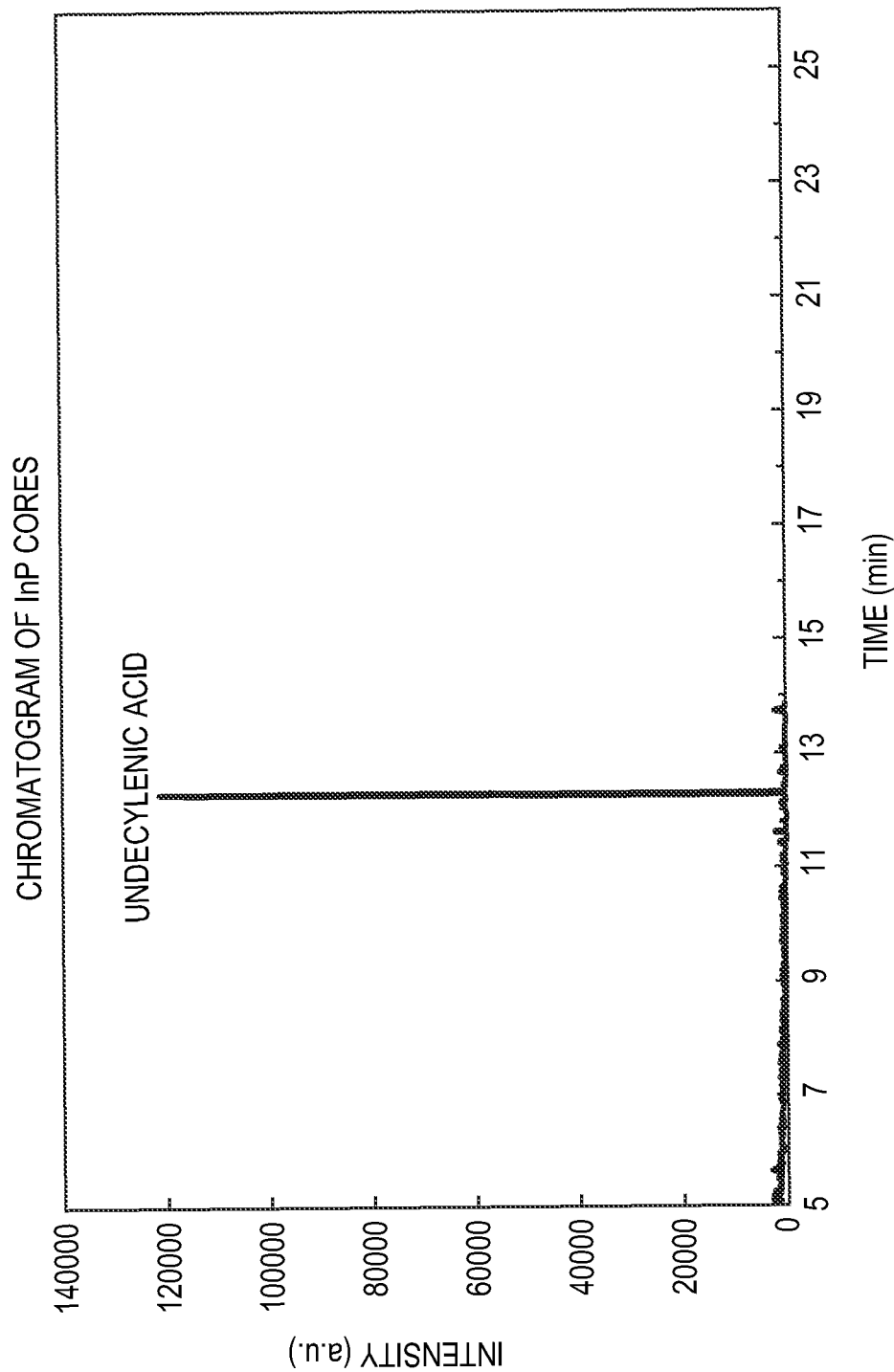
FIG. 6 is a chromatogram of undecylenic acid-capped InP core nanocrystals prepared in Example 7.

Myristic acid (5.125 g), dibutyl sebacate (100 ml) and zinc undecylenate (4.32 g) were mixed together and degassed for 1 h under vacuum at 80° C. in a three-neck round bottom flask containing a stir bar on a heating mantle, and equipped with a thermocouple (and temperature controller). The reaction vessel was backfilled with nitrogen and the solid cluster [Et$_3$NH]$_4$[Zn$_{10}$S$_4$(SPh)$_{16}$] (0.47 g) was added through a side port. The reaction was degassed for 30 minutes under vacuum at 80° C. and during this time the flask was backfilled three times with nitrogen. The reaction was heated to 100° C. and 3 ml of In(MA)$_3$ solution (1M in dibutyl sebacate) was injected dropwise with a glass syringe, followed by 3 ml of P(TMS)$_3$ solution (1M, in dibutyl sebacate). Secondary additions of In(MA)$_3$ and P(TMS)$_3$ solutions were made at 160° C., 190° C., 220° C. and 250° C., until the emission maximum of the particles reached 680 nm. The reaction was cooled at 160° C. and the heating was maintained for 72 h. The reaction was cooled to 30° C. and acetonitrile was added to flocculate the nanocrystals as a red powder. The powder was re-dispersed in chloroform (650 ml) and undecylenic acid (10 g) was added. The resulting solution was loaded in a 200 ml transparent vessel equipped with a stir bar and was etched in air by slow addition of an aqueous solution of HF (5%) under continuous stirring and illumination by light from a 450 W Xenon lamp. The etching process was complete in ~15 hours after which time the InP cores were isolated by addition of methanol and re-dispersed in chloroform (see FIGS. 5 and 6). FIG. 5 is an IR spectrum of the InP core nanocrystals in which can be observed the broad O—H stretch (3500-2500 cm$^{-1}$); C—H stretch (2931-2885 cm$^{-1}$); carboxylic C=O stretch (1641 cm$^{-1}$); and carboxylic C—O stretch (1082 cm$^{-1}$).

PL$_{max}$=611 nm, UV$_{max}$=522 nm, FWHM=65 nm, PLQY=22%, inorganic content by TGA=74%.

Synthesis of InP/ZnS Core/shell

Figure 7:
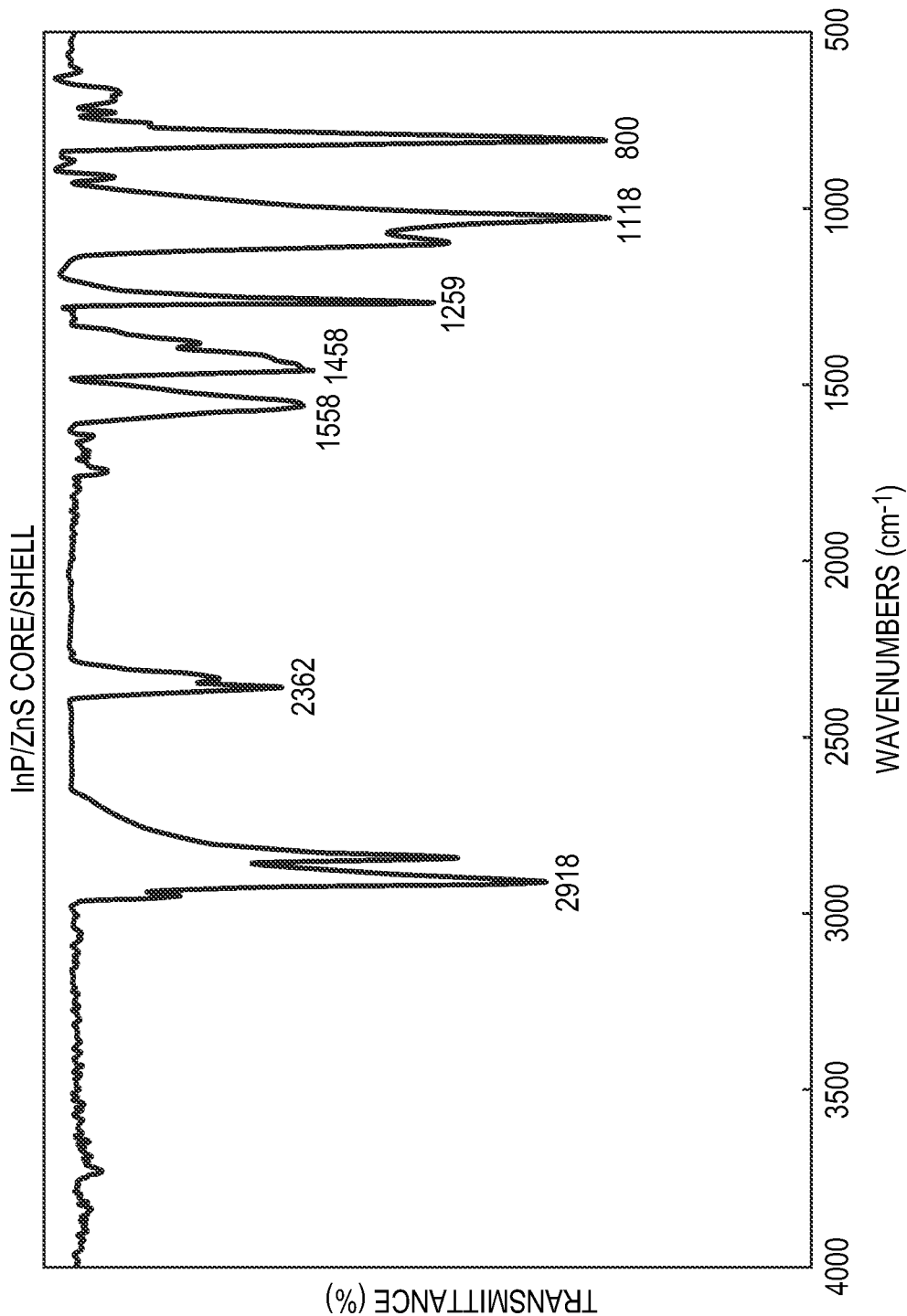
FIG. 7 is an IR spectrum of InP/ZnS core-shell nanocrystals prepared in accordance with an embodiment of the present invention in Example 7.

InP cores in chloroform (100 mg) and therminol (10 ml) were mixed together and degassed for 30 minutes under vacuum at 50° C. in a three-neck round bottom flask containing a stir bar on a heating mantle, and equipped with a thermocouple (and temperature controller). Zinc acetate (380 mg) was added through a side port under a strong nitrogen flow and the resulting mixture was heated to 230° C. in 30 minutes, and held at this temperature for 2 hours. After this time a vinyl thiol compound, 11-mercapto-undecene, (0.5 ml; acting as both the sulfur source for the ZnS shell and the quantum dot surface binding ligand) was mixed with octadecene (0.5 ml) and the resulting solution was injected with a glass syringe. The reaction solution was held at 230° C. for further 1 hour and 30 minutes during which time the luminescence increased substantially. The solution was cooled to 50° C. and the nanocrystals were isolated by addition of a mixture of toluene/acetone/methanol, re-dispersed in toluene and re-precipitated by addition of acetonitrile. The nanocrystals were re-dissolved in anhydrous toluene and stored under nitrogen (see FIGS. 7 and 8). FIG. 7 is an IR spectrum of the InP/ZnS core-shell nanocrystals in which can be observed the C—H stretch (2918 cm$^{-1}$); C=O stretch (1558 cm$^{-1}$); C—O stretch and C=C bend (1200-1118 cm$^{-1}$).

PL$_{max}$=597 nm, FWHM=72 nm, PLQY=54%, UV$_{max}$=536 nm, inorganic content by TGA=55%.

It will be seen that the techniques described herein provide a basis for improved production of nanoparticle materials. The terms and expressions employed herein are used as terms of description and not of limitation, and there is no intention in the use of such terms of and expressions of excluding any equivalents of the features shown and described or portions thereof. Instead, it is recognized that various modifications are possible within the scope of the invention claimed.

What is claimed is:

1. A method for producing surface functionalised nanoparticles comprising:
    reacting first and second nanoparticle precursor species in the presence of a polymeric nanoparticle surface binding ligand having the formula X—Y—Z comprising an alkoxide group and a carboxylate group,
    wherein X is a nanoparticle surface binding group, Y is a linker group, and Z is a functional group, in which Y comprises a polyethyleneglycol group and/or Z comprises an aliphatic group incorporating a terminal unsaturated group, said reaction being effected under conditions permitting binding of said surface binding ligand to growing nanoparticles to produce said surface functionalized nanoparticles.

2. A method according to claim 1, wherein said first nanoparticle precursor species is contacted by said nanoparticle surface binding ligand so as to effect binding of said surface binding ligand to said first nanoparticle precursor species prior to reacting said first nanoparticle precursor species with said second nanoparticle precursor species.

3. A method according to claim 1, wherein during the reaction the first nanoparticle precursor species is added in one or more portions and the second nanoparticle precursor species is added in one or more portions.

4. A method according to claim 3, wherein the first nanoparticle precursor species is added in two or more portions and a temperature of a reaction mixture containing the first and second nanoparticle precursor species and the nanoparticle surface binding ligand is increased between the addition of each portion of the first nanoparticle precursor species.

5. A method according to claim 3, wherein the second nanoparticle precursor species is added in two or more portions and a temperature of a reaction mixture containing the first and second nanoparticle precursor species and the nanoparticle surface binding ligand is increased between the addition of each portion of the second nanoparticle precursor species.

6. A method according to claim 1, wherein the first nanoparticle precursor species is a core nanoparticle and the second nanoparticle precursor species contains a first ion to form at least part of a shell to be deposited on a surface of said core nanoparticle.

7. A method according to claim 1, wherein the second nanoparticle precursor species is a core nanoparticle and the first nanoparticle precursor species contains a first ion to form at least part of a shell to be deposited on a surface of said core nanoparticle.

8. A method according to claim 6 or 7, wherein during the reaction the first nanoparticle precursor species is added in one or more portions and the second nanoparticle precursor species is added in one or more portions.

9. A method according to claim 8, wherein the first nanoparticle precursor species is added in two or more portions and a temperature of a reaction mixture containing the first and second nanoparticle precursor species and the nanoparticle surface binding ligand is increased between the addition of each portion of the first nanoparticle precursor species.

10. A method according to claim 8, wherein the second nanoparticle precursor species is added in two or more portions and a temperature of a reaction mixture containing the first and second nanoparticle precursor species and the nanoparticle surface binding ligand is increased between the addition of each portion of the second nanoparticle precursor species.

11. A method according to claim 6 or 7, wherein the method further comprises reacting said core nanoparticle and said nanoparticle precursor species with a third nanoparticle precursor species containing a second ion to form at least a portion of the shell to be deposited on the surface of said core nanoparticle.

12. A method according to claim 11, wherein during the reaction the third nanoparticle precursor species is added in one or more portions.

13. A method according to claim 12, wherein the third nanoparticle precursor species is added in two or more portions and a temperature of a reaction mixture containing the first, second and third nanoparticle precursor species and the nanoparticle surface binding ligand is increased between the addition of each portion of the third precursor species.

14. A method according to claim 1, wherein the functional group of the surface binding ligand is a charged or polar group, or a crosslinkable or polymerizable group.

15. A method according to claim 1, wherein the functional group of the surface binding ligand is selected from the group consisting of a hydroxide salt, alkoxide salt, carboxylate salt, ammonium salt, sulfonate salt, and phosphate salt.

16. A method according to claim 1, wherein said polymeric compound is a polyether.

17. A method according to claim 1, wherein said terminal unsaturated group is a vinyl group.

18. A method according to claim 1, wherein X comprises at least one carboxylic acid group or at least one thiol group.

19. A method according to claim 1, wherein Y comprises a straight or branched aliphatic group, or an aromatic group.

20. A method according to claim 1, wherein the nanoparticle surface binding ligand is poly(oxyethylene glycol)n monomethyl ether acetic acid with n=1 to 5000.

21. A method for producing surface functionalised nanoparticles comprising:
    reacting first and second nanoparticle precursor species in the presence of a nanoparticle surface binding ligand selected from the group consisting of 10-Undecylenic acid and 11-mercaptoundecene,
    wherein said reaction is effected under conditions permitting binding of said surface binding ligand to growing nanoparticles to produce said surface functionalized nanoparticles.

22. A method for producing surface functionalised nanoparticles comprising:
    reacting first and second nanoparticle precursor species in the presence of a nanoparticle surface binding ligand having the formula

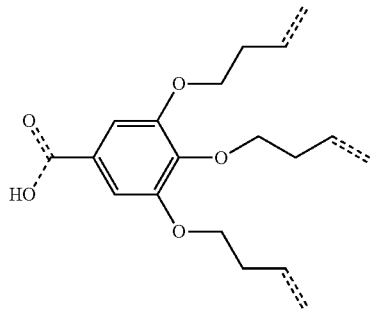

wherein said reaction is effected under conditions permitting binding of said surface binding ligand to growing nanoparticles to produce said surface functionalized nanoparticles.

* * * * *